US010646485B2

(12) United States Patent
Saim et al.

(10) Patent No.: US 10,646,485 B2
(45) Date of Patent: *May 12, 2020

(54) PROCESS OF MAKING STABLE ABUSE-DETERRENT ORAL FORMULATIONS

(71) Applicant: Collegium Pharmaceutical, Inc., Stoughton, MA (US)

(72) Inventors: Said Saim, Wrentham, MA (US); Alison B. Fleming, Mansfield, MA (US); Ravi K. Varanasi, Walpole, MA (US)

(73) Assignee: Collegium Pharmaceutical, Inc., Stoughton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/218,801

(22) Filed: Dec. 13, 2018

(65) Prior Publication Data

US 2019/0255038 A1 Aug. 22, 2019

Related U.S. Application Data

(63) Continuation of application No. 15/950,656, filed on Apr. 11, 2018, now Pat. No. 10,188,644, which is a (Continued)

(51) Int. Cl.
*A61K 31/485* (2006.01)
*A61K 47/12* (2006.01)
(Continued)

(52) U.S. Cl.
CPC .......... *A61K 31/485* (2013.01); *A61K 9/1617* (2013.01); *A61K 9/1694* (2013.01);
(Continued)

(58) Field of Classification Search
None
See application file for complete search history.

(56) References Cited

U.S. PATENT DOCUMENTS

| 1,349,326 A | 8/1920 | Davis |
| 2,404,319 A | 7/1946 | Shelton |
| (Continued) | | |

FOREIGN PATENT DOCUMENTS

| CA | 2273808 A1 | 9/2000 |
| EP | 0179583 A1 | 4/1986 |
| (Continued) | | |

OTHER PUBLICATIONS

[Author Unknown], "OxyContin Diversion and Abuse." Department of Justice, National Drug Intelligence Center, Information Bulletin, Jan. 2001; 3 pages, https://www.justice.gov/archive/ndic//pubs/651/abuse.htm.

(Continued)

*Primary Examiner* — Robert A Wax
*Assistant Examiner* — Melissa S Mercier
(74) *Attorney, Agent, or Firm* — Cooley LLP

(57) ABSTRACT

The present disclosure relates to cured pharmaceutical compositions designed to reduce the potential for improper administration of drugs that are subject to abuse, the process of curing such composition in order to improve the dissolution stability, method of using the same for treatment of pain.

67 Claims, 11 Drawing Sheets

Figure 1:
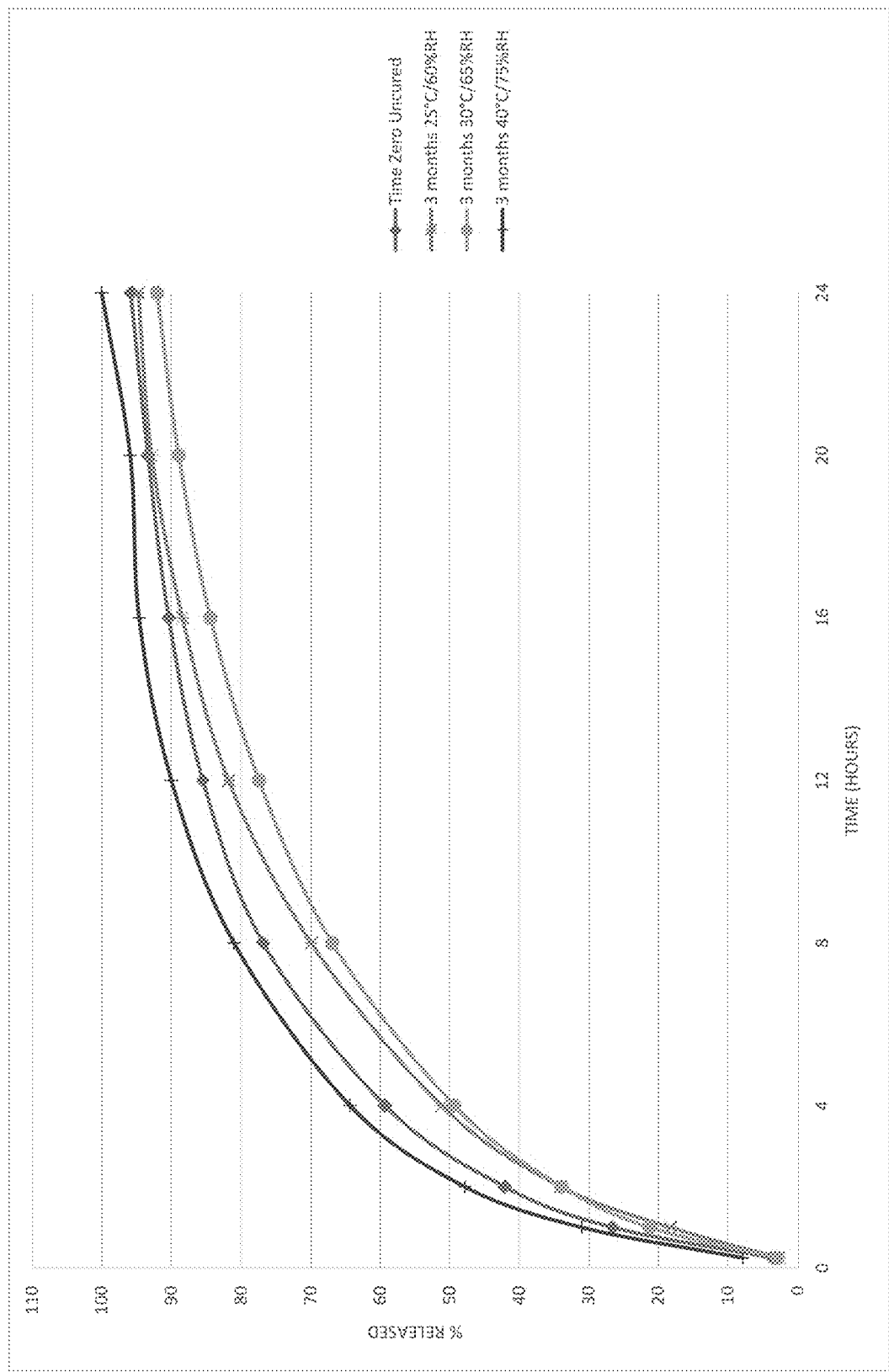

Related U.S. Application Data continuation of application No. 15/649,024, filed on Jul. 13, 2017, now Pat. No. 9,968,598, which is a continuation of application No. 15/255,859, filed on Sep. 2, 2016, now Pat. No. 9,737,530.

(60) Provisional application No. 62/353,839, filed on Jun. 23, 2016.

(51) Int. Cl.
*A61K 47/44* (2017.01)
*A61K 47/26* (2006.01)
*A61K 9/48* (2006.01)
*A61K 9/16* (2006.01)

(52) U.S. Cl.
CPC .......... *A61K 9/4808* (2013.01); *A61K 9/4833* (2013.01); *A61K 9/4858* (2013.01); *A61K 9/4875* (2013.01); *A61K 47/12* (2013.01); *A61K 47/26* (2013.01); *A61K 47/44* (2013.01)

(56) References Cited

U.S. PATENT DOCUMENTS

| | | |
|---|---|---|
| 3,015,128 A | 1/1962 | Somerville, Jr. |
| 3,065,143 A | 11/1962 | Christenson et al. |
| 3,133,132 A | 5/1964 | Loeb et al. |
| 3,146,167 A | 8/1964 | Lantz, Jr. et al. |
| 3,172,816 A | 3/1965 | Swintosky et al. |
| 3,173,876 A | 3/1965 | Zobrist et al. |
| 3,260,646 A | 7/1966 | Paulsen |
| 3,276,586 A | 10/1966 | Rosaen |
| 3,336,200 A | 8/1967 | Krause et al. |
| 3,402,240 A | 9/1968 | Cain et al. |
| 3,541,005 A | 11/1970 | Strathmann et al. |
| 3,541,006 A | 11/1970 | Bixler et al. |
| 3,546,876 A | 12/1970 | Fokker et al. |
| 3,773,955 A | 11/1973 | Pachter et al. |
| 3,845,770 A | 11/1974 | Theeuwes et al. |
| 3,879,555 A | 4/1975 | Pachter et al. |
| 3,916,889 A | 11/1975 | Russell |
| 3,965,256 A | 6/1976 | Leslie |
| 3,966,940 A | 6/1976 | Pachter et al. |
| 3,980,766 A | 9/1976 | Shaw et al. |
| 4,063,064 A | 12/1977 | Saunders et al. |
| 4,070,494 A | 1/1978 | Hoffmeister et al. |
| 4,088,864 A | 5/1978 | Theeuwes et al. |
| 4,098,575 A | 7/1978 | Matsushita |
| 4,132,753 A | 1/1979 | Blichare et al. |
| 4,160,020 A | 7/1979 | Ayer et al. |
| 4,175,119 A | 11/1979 | Porter |
| 4,200,098 A | 4/1980 | Ayer et al. |
| 4,235,870 A | 11/1980 | Leslie |
| 4,285,987 A | 8/1981 | Ayer et al. |
| 4,293,539 A | 10/1981 | Ludwig et al. |
| 4,366,310 A | 12/1982 | Leslie |
| 4,385,057 A | 5/1983 | Bjork et al. |
| 4,389,393 A | 6/1983 | Schor et al. |
| 4,424,205 A | 1/1984 | LaHann et al. |
| 4,443,428 A | 4/1984 | Oshlack et al. |
| 4,457,933 A | 7/1984 | Gordon et al. |
| 4,459,278 A | 7/1984 | Porter |
| 4,483,847 A | 11/1984 | Augart |
| 4,569,937 A | 2/1986 | Baker et al. |
| 4,588,580 A | 5/1986 | Gale et al. |
| 4,599,326 A | 7/1986 | Marvola et al. |
| 4,599,342 A | 7/1986 | LaHann |
| 4,610,870 A | 9/1986 | Jain et al. |
| 4,612,008 A | 9/1986 | Wong et al. |
| 4,629,623 A | 12/1986 | Balazs et al. |
| 4,661,492 A | 4/1987 | Lewis et al. |
| 4,666,705 A | 5/1987 | Decrosta et al. |
| 4,675,140 A | 6/1987 | Sparks et al. |
| 4,710,384 A | 12/1987 | Rotman |
| 4,713,243 A | 12/1987 | Schiraldi et al. |
| 4,722,941 A | 2/1988 | Eckert et al. |
| 4,737,151 A | 4/1988 | Clement et al. |
| 4,764,378 A | 8/1988 | Keith et al. |
| 4,765,989 A | 8/1988 | Wong et al. |
| 4,769,372 A | 9/1988 | Kreek |
| 4,785,000 A | 11/1988 | Kreek et al. |
| 4,806,341 A | 2/1989 | Chien et al. |
| 4,812,446 A | 3/1989 | Brand |
| 4,834,984 A | 5/1989 | Goldie et al. |
| 4,844,909 A | 7/1989 | Goldie et al. |
| 4,861,598 A | 8/1989 | Oshlack |
| 4,869,904 A | 9/1989 | Uekama et al. |
| 4,957,681 A | 9/1990 | Klimesch et al. |
| 4,970,075 A | 11/1990 | Oshlack |
| 4,990,341 A | 2/1991 | Goldie et al. |
| 4,992,277 A | 2/1991 | Sangekar et al. |
| 5,026,556 A | 6/1991 | Drust et al. |
| 5,059,600 A | 10/1991 | Gawin et al. |
| 5,069,909 A | 12/1991 | Sharma et al. |
| 5,111,942 A | 5/1992 | Bernardin |
| 5,113,585 A | 5/1992 | Rogers et al. |
| 5,114,942 A | 5/1992 | Gawin et al. |
| 5,130,311 A | 7/1992 | Guillaumet et al. |
| 5,139,790 A | 8/1992 | Snipes |
| 5,149,538 A | 9/1992 | Granger et al. |
| 5,169,645 A | 12/1992 | Shukla et al. |
| 5,183,654 A | 2/1993 | Speck et al. |
| 5,190,947 A | 3/1993 | Riess et al. |
| 5,202,128 A | 4/1993 | Morella et al. |
| 5,215,758 A | 6/1993 | Krishnamurthy |
| 5,225,199 A | 7/1993 | Hidaka et al. |
| 5,232,685 A | 8/1993 | Speck et al. |
| 5,232,934 A | 8/1993 | Downs |
| 5,240,711 A | 8/1993 | Hille et al. |
| 5,266,331 A | 11/1993 | Oshlack et al. |
| 5,273,758 A | 12/1993 | Royce |
| 5,273,760 A | 12/1993 | Oshlack |
| 5,283,065 A | 2/1994 | Doyon et al. |
| 5,286,493 A | 2/1994 | Oshlack et al. |
| 5,290,816 A | 3/1994 | Blumberg |
| 5,300,302 A | 4/1994 | Tachon et al. |
| 5,321,012 A | 6/1994 | Mayer et al. |
| 5,324,351 A | 6/1994 | Oshlack et al. |
| 5,330,766 A | 7/1994 | Morella et al. |
| 5,354,863 A | 10/1994 | Dappen et al. |
| 5,356,467 A | 10/1994 | Oshlack et al. |
| 5,376,705 A | 12/1994 | Leys et al. |
| 5,378,474 A | 1/1995 | Morella et al. |
| 5,399,351 A | 3/1995 | Leschiner et al. |
| 5,403,868 A | 4/1995 | Reid et al. |
| 5,409,944 A | 4/1995 | Black et al. |
| 5,411,745 A | 5/1995 | Oshlack et al. |
| 5,422,123 A | 6/1995 | Conte et al. |
| 5,422,134 A | 6/1995 | Hart et al. |
| 5,436,265 A | 7/1995 | Black et al. |
| 5,460,826 A | 10/1995 | Merrill et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,500,227 A | 3/1996 | Oshlack et al. |
| 5,502,058 A | 3/1996 | Mayer et al. |
| 5,505,959 A | 4/1996 | Tachon et al. |
| 5,508,042 A | 4/1996 | Oshlack et al. |
| 5,508,043 A | 4/1996 | Krishnamurthy |
| 5,510,368 A | 4/1996 | Lau et al. |
| 5,514,680 A | 5/1996 | Weber et al. |
| 5,521,213 A | 5/1996 | Prasit et al. |
| 5,536,752 A | 7/1996 | Ducharme et al. |
| 5,545,628 A | 8/1996 | Deboeck |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,580,578 A | 12/1996 | Oshlack et al. |
| 5,582,837 A | 12/1996 | Shell |
| 5,593,695 A | 1/1997 | Merrill et al. |
| 5,593,994 A | 1/1997 | Batt et al. |
| 5,604,253 A | 2/1997 | Lau et al. |

(56) References Cited

U.S. PATENT DOCUMENTS

| | | |
|---|---|---|
| 5,604,260 A | 2/1997 | Guay et al. |
| 5,616,601 A | 4/1997 | Khanna et al. |
| 5,635,159 A | 6/1997 | Fu Lu et al. |
| 5,639,476 A | 6/1997 | Oshlack et al. |
| 5,639,789 A | 6/1997 | Lau et al. |
| 5,656,295 A | 8/1997 | Oshlack et al. |
| 5,667,805 A | 9/1997 | Merrill et al. |
| 5,672,360 A | 9/1997 | Sackler et al. |
| 5,679,650 A | 10/1997 | Fukunaga et al. |
| 5,681,585 A | 10/1997 | Oshlack et al. |
| 5,695,781 A | 12/1997 | Zhang et al. |
| 5,700,410 A | 12/1997 | Nakamichi et al. |
| 5,702,725 A | 12/1997 | Merrill et al. |
| 5,730,716 A | 3/1998 | Beck et al. |
| 5,741,524 A | 4/1998 | Staniforth et al. |
| 5,756,123 A | 5/1998 | Yamamoto et al. |
| 5,756,483 A | 5/1998 | Merkus |
| 5,762,963 A | 6/1998 | Byas-Smith |
| 5,766,623 A | 6/1998 | Aryes et al. |
| 5,811,126 A | 9/1998 | Krishnamurthy |
| 5,843,480 A | 12/1998 | Miller et al. |
| 5,849,240 A | 12/1998 | Miller et al. |
| 5,866,161 A | 2/1999 | Childers et al. |
| 5,866,164 A | 2/1999 | Kuczynski et al. |
| 5,879,705 A | 3/1999 | Heafield et al. |
| 5,891,471 A | 4/1999 | Miller et al. |
| 5,891,919 A | 4/1999 | Blum et al. |
| 5,914,129 A | 6/1999 | Mauskop |
| 5,914,131 A | 6/1999 | Miller et al. |
| 5,948,787 A | 9/1999 | Merrill et al. |
| 5,952,005 A | 9/1999 | Olsson et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 6,008,355 A | 12/1999 | Huang et al. |
| 6,024,982 A | 2/2000 | Oshlack et al. |
| 6,048,736 A | 4/2000 | Kosak |
| 6,068,855 A | 5/2000 | Leslie et al. |
| 6,096,722 A | 8/2000 | Bennett et al. |
| 6,103,261 A | 8/2000 | Chasin et al. |
| 6,120,751 A | 9/2000 | Unger |
| 6,124,282 A | 9/2000 | Sellers et al. |
| 6,126,969 A | 10/2000 | Shah et al. |
| 6,136,864 A | 10/2000 | Nichols et al. |
| 6,143,322 A | 11/2000 | Sackler et al. |
| 6,153,621 A | 11/2000 | Hamann |
| 6,156,764 A | 12/2000 | Asmussen et al. |
| 6,162,467 A | 12/2000 | Miller et al. |
| 6,177,567 B1 | 1/2001 | Chiu et al. |
| 6,210,712 B1 | 4/2001 | Edgren et al. |
| 6,210,714 B1 | 4/2001 | Oshlack et al. |
| 6,223,075 B1 | 4/2001 | Beck et al. |
| 6,228,863 B1 | 5/2001 | Palermo et al. |
| 6,245,357 B1 | 6/2001 | Edaren et al. |
| 6,248,363 B1 | 6/2001 | Patel et al. |
| 6,251,430 B1 | 6/2001 | Zhang et al. |
| 6,255,502 B1 | 7/2001 | Penkler et al. |
| 6,261,599 B1 | 7/2001 | Oshlack et al. |
| 6,267,985 B1 | 7/2001 | Chen et al. |
| 6,277,384 B1 | 8/2001 | Kaiko et al. |
| 6,277,398 B1 | 8/2001 | Caruso |
| 6,290,990 B1 | 9/2001 | Grabowski et al. |
| 6,294,194 B1 | 9/2001 | Horhota et al. |
| 6,294,195 B1 | 9/2001 | Oshlack et al. |
| 6,309,663 B1 | 10/2001 | Patel et al. |
| 6,309,668 B1 | 10/2001 | Bastin et al. |
| 6,310,072 B1 | 10/2001 | Smith et al. |
| 6,312,704 B1 | 11/2001 | Farah et al. |
| 6,328,979 B1 | 12/2001 | Yamashita et al. |
| 6,335,033 B2 | 1/2002 | Oshlack et al. |
| 6,344,212 B2 | 2/2002 | Reder et al. |
| 6,348,469 B1 | 2/2002 | Seth |
| 6,352,721 B1 | 3/2002 | Faour |
| 6,375,957 B1 | 4/2002 | Kaiko et al. |
| 6,379,707 B2 | 4/2002 | Vladyka, Jr. et al. |
| 6,403,056 B1 | 6/2002 | Unger |
| 6,419,954 B1 | 7/2002 | Chu |
| 6,436,441 B1 | 8/2002 | Sako et al. |
| 6,440,464 B1 | 8/2002 | Hsia et al. |
| 6,468,559 B1 | 10/2002 | Chen et al. |
| 6,468,560 B2 | 10/2002 | Sauer et al. |
| 6,475,494 B2 | 11/2002 | Kaiko et al. |
| 6,488,963 B1 | 12/2002 | McGinity et al. |
| 6,491,949 B2 | 12/2002 | Faour et al. |
| 6,552,031 B1 | 4/2003 | Burch et al. |
| 6,559,159 B2 | 5/2003 | Carroll et al. |
| 6,572,885 B2 | 6/2003 | Oshlack et al. |
| 6,593,367 B1 | 7/2003 | Dewey et al. |
| 6,627,635 B2 | 9/2003 | Palermo et al. |
| 6,645,527 B2 | 11/2003 | Oshlack et al. |
| 6,692,767 B2 | 2/2004 | Burnside et al. |
| 6,696,088 B2 | 2/2004 | Oshlack et al. |
| 6,706,281 B2 | 3/2004 | Oshlack et al. |
| 6,723,343 B2 | 4/2004 | Kugelmann |
| 6,733,783 B2 | 5/2004 | Oshlack et al. |
| 6,743,442 B2 | 6/2004 | Oshlack et al. |
| 6,808,720 B2 | 10/2004 | Unger |
| 6,919,372 B1 | 7/2005 | Yamashita et al. |
| 6,984,403 B2 | 1/2006 | Hagen et al. |
| 6,995,169 B2 | 2/2006 | Chapleo et al. |
| 7,011,846 B2 | 3/2006 | Shojaei et al. |
| 7,141,250 B2 | 11/2006 | Oshlack et al. |
| 7,144,587 B2 | 12/2006 | Oshlack et al. |
| 7,157,103 B2 | 1/2007 | Sackler |
| 7,201,920 B2 | 4/2007 | Kumar et al. |
| 7,261,529 B2 | 8/2007 | Persyn et al. |
| 7,276,250 B2 | 10/2007 | Baichwal et al. |
| 7,332,182 B2 | 2/2008 | Sackler |
| 7,399,488 B2 | 7/2008 | Hirsh et al. |
| 7,510,726 B2 | 3/2009 | Kumar et al. |
| 7,670,612 B2 | 3/2010 | Miller |
| 7,727,557 B2 | 6/2010 | Sackler |
| 7,771,707 B2 | 8/2010 | Hirsh et al. |
| 7,776,314 B2 | 8/2010 | Bartholomaus |
| 7,842,307 B2 | 11/2010 | Oshlack et al. |
| 7,943,174 B2 | 5/2011 | Oshlack et al. |
| 7,981,439 B2 | 7/2011 | Kumar et al. |
| 8,017,148 B2 | 9/2011 | Sackler |
| 8,075,872 B2 | 12/2011 | Arkenau-Maric et al. |
| 8,101,630 B2 | 1/2012 | Kumar et al. |
| 8,114,383 B2 | 2/2012 | Bartholomaus |
| 8,114,384 B2 | 2/2012 | Arkenau et al. |
| 8,192,722 B2 | 6/2012 | Arkenau-Maric et al. |
| 8,309,060 B2 | 11/2012 | Bartholomaus et al. |
| 8,337,888 B2 | 12/2012 | Wright et al. |
| 8,389,007 B2 | 3/2013 | Wright et al. |
| 8,409,616 B2 | 4/2013 | Kumar et al. |
| 8,449,909 B2 | 5/2013 | Hirsh et al. |
| 8,524,275 B2 | 9/2013 | Oshlack et al. |
| 8,529,948 B1 | 9/2013 | Wright et al. |
| 8,557,291 B2 | 10/2013 | Rariy et al. |
| 8,569,228 B2 | 10/2013 | Jenkins et al. |
| 8,609,683 B2 | 12/2013 | Wright et al. |
| 8,637,540 B2 | 1/2014 | Kumar et al. |
| 8,652,497 B2 | 2/2014 | Sackler |
| 8,652,515 B2 | 2/2014 | Sackler |
| 8,758,813 B2 | 6/2014 | Hirsh et al. |
| 8,840,928 B2 | 9/2014 | Rariy et al. |
| 8,871,265 B2 | 10/2014 | Wright et al. |
| 8,932,628 B2 | 1/2015 | Oberegger et al. |
| 8,999,961 B2 | 4/2015 | Wright et al. |
| 9,034,376 B2 | 5/2015 | Wright et al. |
| 9,040,084 B2 | 5/2015 | Wright et al. |
| 9,044,398 B2 | 6/2015 | Hirsh et al. |
| 9,044,435 B2 | 6/2015 | Wright et al. |
| 9,060,976 B2 | 6/2015 | Wright et al. |
| 9,155,717 B2 | 10/2015 | Sackler |
| 9,248,195 B2 | 2/2016 | Rariy et al. |
| 9,308,170 B2 | 4/2016 | Wright et al. |
| 9,308,171 B2 | 4/2016 | Wright et al. |
| 9,387,173 B2 | 7/2016 | Wright et al. |
| 9,387,174 B2 | 7/2016 | Wright et al. |

(56) References Cited

U.S. PATENT DOCUMENTS

| | | |
|---|---|---|
| 9,592,200 B2 | 3/2017 | Rariy et al. |
| 9,682,075 B2 | 6/2017 | Rariy et al. |
| 9,693,961 B2 | 7/2017 | Wright et al. |
| 9,737,530 B1* | 8/2017 | Saim ................. A61K 31/485 |
| 9,763,883 B2 | 9/2017 | Hirsh et al. |
| 9,968,598 B2* | 5/2018 | Saim ................. A61K 31/485 |
| 10,004,729 B2 | 6/2018 | Rariy et al. |
| 10,188,644 B2* | 1/2019 | Saim ................. A61K 31/485 |
| 10,206,881 B2 | 2/2019 | Wright et al. |
| 10,525,052 B2 | 1/2020 | Hirsh et al. |
| 10,525,053 B2 | 1/2020 | Rariy et al. |
| 2001/0006650 A1 | 7/2001 | Burnside et al. |
| 2001/0031278 A1 | 10/2001 | Oshlack et al. |
| 2001/0036476 A1 | 11/2001 | Oshlack et al. |
| 2002/0032166 A1 | 3/2002 | Shefter et al. |
| 2002/0036154 A1 | 3/2002 | Murari et al. |
| 2002/0081333 A1 | 6/2002 | Oshlack et al. |
| 2002/0131988 A1 | 9/2002 | Foster et al. |
| 2002/0142039 A1 | 10/2002 | Claude |
| 2002/0187192 A1 | 12/2002 | Joshi et al. |
| 2003/0004177 A1 | 1/2003 | Kao et al. |
| 2003/0021841 A1 | 1/2003 | Matharu et al. |
| 2003/0026838 A1 | 2/2003 | Farrell |
| 2003/0035839 A1 | 2/2003 | Hirsh et al. |
| 2003/0044446 A1 | 3/2003 | Moro et al. |
| 2003/0059397 A1 | 3/2003 | Hughes |
| 2003/0059471 A1 | 3/2003 | Compton et al. |
| 2003/0064099 A1 | 4/2003 | Oshlack et al. |
| 2003/0064122 A1 | 4/2003 | Goldberg et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0082230 A1 | 5/2003 | Baichwal et al. |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0126428 A1 | 7/2003 | Liu et al. |
| 2003/0170181 A1 | 9/2003 | Midha |
| 2003/0232081 A1 | 12/2003 | Doshi et al. |
| 2004/0010000 A1 | 1/2004 | Ayer et al. |
| 2004/0047907 A1 | 3/2004 | Oshlack et al. |
| 2004/0052731 A1 | 3/2004 | Hirsh et al. |
| 2004/0062778 A1 | 4/2004 | Shefer et al. |
| 2004/0126428 A1 | 7/2004 | Hughes et al. |
| 2004/0131552 A1 | 7/2004 | Boehm |
| 2004/0151791 A1 | 8/2004 | Mato-Alvarez et al. |
| 2004/0170680 A1 | 9/2004 | Oshlack et al. |
| 2004/0224020 A1 | 11/2004 | Schoenhard |
| 2004/0228802 A1 | 11/2004 | Chang et al. |
| 2004/0241234 A1 | 12/2004 | Vikov |
| 2004/0253310 A1 | 12/2004 | Fischer et al. |
| 2004/0266807 A1 | 12/2004 | Oshlack et al. |
| 2005/0013862 A1 | 1/2005 | Tobyn et al. |
| 2005/0020613 A1 | 1/2005 | Boehm et al. |
| 2005/0031546 A1 | 2/2005 | Bartholomaus et al. |
| 2005/0063909 A1 | 3/2005 | Wright et al. |
| 2005/0106249 A1 | 5/2005 | Hwang et al. |
| 2005/0112067 A1 | 5/2005 | Kumar et al. |
| 2005/0112201 A1 | 5/2005 | Baichwal et al. |
| 2005/0118267 A1 | 6/2005 | Baichwal et al. |
| 2005/0158382 A1 | 7/2005 | Cruz et al. |
| 2005/0163717 A1 | 7/2005 | Anderson et al. |
| 2005/0181050 A1 | 8/2005 | Hirsh et al. |
| 2005/0186139 A1 | 8/2005 | Bartholomaeus et al. |
| 2005/0186285 A1 | 8/2005 | Ray et al. |
| 2005/0214223 A1 | 9/2005 | Bartholomaeus et al. |
| 2005/0236741 A1 | 10/2005 | Arkenau et al. |
| 2005/0276853 A1 | 12/2005 | Baichwal et al. |
| 2005/0281748 A1 | 12/2005 | Hirsh et al. |
| 2006/0002860 A1 | 1/2006 | Bartholomaus et al. |
| 2006/0018837 A1 | 1/2006 | Preston et al. |
| 2006/0039864 A1 | 2/2006 | Bartholomaus et al. |
| 2006/0104909 A1 | 5/2006 | Vaghefi et al. |
| 2006/0110457 A1 | 5/2006 | Labrecque et al. |
| 2006/0111383 A1 | 5/2006 | Casner et al. |
| 2006/0165790 A1 | 7/2006 | Walden et al. |
| 2006/0188447 A1 | 8/2006 | Arkenau-Maric et al. |
| 2006/0193782 A1 | 8/2006 | Bartholomaus et al. |
| 2006/0251721 A1 | 11/2006 | Cruz et al. |
| 2007/0003616 A1 | 1/2007 | Arkenau-Maric et al. |
| 2007/0003617 A1 | 1/2007 | Fischer et al. |
| 2007/0054002 A1 | 3/2007 | Persyn et al. |
| 2007/0110807 A1 | 5/2007 | Vergnault et al. |
| 2007/0166234 A1 | 7/2007 | Kumar et al. |
| 2007/0264327 A1 | 11/2007 | Kumar et al. |
| 2008/0063725 A1 | 3/2008 | Guimbertau et al. |
| 2008/0095843 A1 | 4/2008 | Nutalapati et al. |
| 2008/0176955 A1 | 7/2008 | Heck et al. |
| 2008/0199530 A1 | 8/2008 | Hirsh et al. |
| 2008/0254123 A1 | 10/2008 | Fischer et al. |
| 2008/0260815 A1 | 10/2008 | Haves et al. |
| 2008/0260819 A1 | 10/2008 | Fleming et al. |
| 2009/0081290 A1 | 3/2009 | McKenna et al. |
| 2009/0142378 A1 | 6/2009 | Frisbee |
| 2009/0169587 A1 | 7/2009 | Baichwal et al. |
| 2009/0215808 A1 | 8/2009 | Yum et al. |
| 2009/0297617 A1* | 12/2009 | Rariy ................. A61K 9/1617 424/490 |
| 2010/0216829 A2 | 8/2010 | Kumar et al. |
| 2010/0221293 A1 | 9/2010 | Cruz et al. |
| 2010/0260834 A1 | 10/2010 | Hirsh et al. |
| 2011/0142943 A1 | 6/2011 | Rariy et al. |
| 2011/0262532 A1 | 10/2011 | Oshlack et al. |
| 2012/0164220 A1 | 6/2012 | Huang |
| 2013/0045960 A1 | 2/2013 | Hirsh et al. |
| 2013/0217716 A1 | 8/2013 | Wright et al. |
| 2013/0245055 A1 | 9/2013 | Wright et al. |
| 2013/0310413 A1 | 11/2013 | Hirsh et al. |
| 2014/0105987 A1 | 4/2014 | Rariy et al. |
| 2014/0121232 A1 | 5/2014 | Hirsh et al. |
| 2014/0213606 A1 | 7/2014 | Wright et al. |
| 2014/0271835 A1 | 9/2014 | Wengner |
| 2014/0371257 A1 | 12/2014 | Wright et al. |
| 2015/0004244 A1 | 1/2015 | Rariy et al. |
| 2015/0005331 A1 | 1/2015 | Wright et al. |
| 2015/0005332 A1 | 1/2015 | Rariy et al. |
| 2015/0031718 A1 | 1/2015 | Wright et al. |
| 2015/0140083 A1 | 5/2015 | Wright et al. |
| 2015/0147391 A1 | 5/2015 | Wright et al. |
| 2015/0148319 A1 | 5/2015 | Wright et al. |
| 2015/0164835 A1 | 6/2015 | King et al. |
| 2015/0182628 A1 | 7/2015 | Wright et al. |
| 2015/0238481 A1 | 8/2015 | Wright et al. |
| 2015/0265596 A1 | 9/2015 | Hirsh et al. |
| 2015/0265602 A1 | 9/2015 | Wright et al. |
| 2015/0265603 A1 | 9/2015 | Wright et al. |
| 2015/0265604 A1 | 9/2015 | Wright et al. |
| 2015/0265605 A1 | 9/2015 | Wright et al. |
| 2015/0265606 A1 | 9/2015 | Wright et al. |
| 2015/0265607 A1 | 9/2015 | Wright et al. |
| 2015/0273064 A1 | 10/2015 | Wright et al. |
| 2015/0273065 A1 | 10/2015 | Wright et al. |
| 2015/0283128 A1 | 10/2015 | Wright et al. |
| 2015/0283129 A1 | 10/2015 | Wright et al. |
| 2015/0283130 A1 | 10/2015 | Wright et al. |
| 2015/0283250 A1 | 10/2015 | Wright et al. |
| 2015/0374628 A1 | 12/2015 | Wright et al. |
| 2015/0374631 A1 | 12/2015 | Wright et al. |
| 2016/0000712 A1 | 1/2016 | Wright et al. |
| 2016/0000717 A1 | 1/2016 | Wright et al. |
| 2016/0000718 A1 | 1/2016 | Wright et al. |
| 2016/0000719 A1 | 1/2016 | Wright et al. |
| 2016/0000776 A1 | 1/2016 | Wright et al. |
| 2016/0058716 A1 | 3/2016 | Wright et al. |
| 2016/0074326 A1 | 3/2016 | Rariy et al. |
| 2016/0151277 A1 | 6/2016 | Wright et al. |
| 2016/0151289 A1 | 6/2016 | Wright et al. |
| 2016/0151290 A1 | 6/2016 | Wright et al. |
| 2016/0151291 A1 | 6/2016 | Wright et al. |
| 2016/0151297 A1 | 6/2016 | Wright et al. |
| 2016/0151355 A1 | 6/2016 | Wright et al. |
| 2016/0151356 A1 | 6/2016 | Wright et al. |

(56) References Cited

U.S. PATENT DOCUMENTS

| | | |
|---|---|---|
| 2016/0151357 A1 | 6/2016 | Wright et al. |
| 2016/0151358 A1 | 6/2016 | Wright et al. |
| 2016/0151360 A1 | 6/2016 | Wright et al. |
| 2016/0151499 A1 | 6/2016 | Wright et al. |
| 2016/0151502 A1 | 6/2016 | Wright et al. |
| 2017/0020863 A1 | 1/2017 | Wright et al. |
| 2017/0020864 A1 | 1/2017 | Wright et al. |
| 2017/0065524 A1 | 3/2017 | Wright et al. |
| 2017/0065525 A1 | 3/2017 | Wright et al. |
| 2017/0112765 A1 | 4/2017 | Wright et al. |
| 2017/0182032 A1 | 6/2017 | Rariy et al. |
| 2017/0296533 A1 | 10/2017 | Wright et al. |
| 2017/0319575 A1 | 11/2017 | Rariy et al. |
| 2017/0360710 A1 | 12/2017 | Hirsh et al. |
| 2017/0368057 A1 | 12/2017 | Saim et al. |
| 2018/0028528 A1 | 2/2018 | Hirsh et al. |
| 2018/0028529 A1 | 2/2018 | Rariy et al. |
| 2018/0125788 A1 | 5/2018 | Wright et al. |
| 2018/0147151 A1 | 5/2018 | Wright et al. |
| 2018/0289697 A1 | 10/2018 | Saim et al. |
| 2018/0369236 A1 | 12/2018 | Rariy et al. |
| 2019/0167662 A1 | 6/2019 | Rariy et al. |
| 2019/0262335 A1 | 8/2019 | Rariy et al. |

FOREIGN PATENT DOCUMENTS

| | | |
|---|---|---|
| EP | 0253104 A1 | 1/1988 |
| EP | 318262 | 5/1989 |
| EP | 0375063 A1 | 6/1990 |
| EP | 0578231 A1 | 1/1994 |
| EP | 0647448 A1 | 4/1995 |
| EP | 0661045 | 5/1995 |
| EP | 0 661 045 A1 | 7/1995 |
| EP | 0698389 | 2/1996 |
| EP | 0 974 345 | 1/2000 |
| EP | 1293195 | 3/2003 |
| EP | 0 828 802 | 6/2003 |
| GB | 1513166 A | 6/1978 |
| GB | 2162061 A | 1/1986 |
| WO | WO 91/07950 | 6/1991 |
| WO | WO 1993/10765 | 6/1993 |
| WO | WO 1993/010765 A1 | 6/1993 |
| WO | WO 95/18602 | 7/1995 |
| WO | WO 95/20947 | 8/1995 |
| WO | WO 1995/020947 A1 | 8/1995 |
| WO | WO 96/06528 | 3/1996 |
| WO | WO 97/12605 | 4/1997 |
| WO | WO 1997/014438 A1 | 4/1997 |
| WO | WO 97/37689 | 10/1997 |
| WO | WO 97/48385 | 12/1997 |
| WO | WO 97/49384 | 12/1997 |
| WO | WO 1997/049384 A1 | 12/1997 |
| WO | WO 1997/049402 A1 | 12/1997 |
| WO | WO 1998/002187 A1 | 1/1998 |
| WO | WO 1998/018827 A1 | 5/1998 |
| WO | WO 1999/001111 A1 | 1/1999 |
| WO | WO 99/20255 | 4/1999 |
| WO | WO 99/32119 | 7/1999 |
| WO | WO 99/32120 | 7/1999 |
| WO | WO 1999/042086 A1 | 8/1999 |
| WO | WO 99/44591 | 9/1999 |
| WO | WO 1999/63971 A1 | 12/1999 |
| WO | WO 2000/033835 | 6/2000 |
| WO | WO 2000/38649 A1 | 7/2000 |
| WO | WO 2000/050071 A1 | 8/2000 |
| WO | WO 2001/008661 A2 | 2/2001 |
| WO | WO 2001/058447 | 8/2001 |
| WO | WO 2001/058447 A1 | 8/2001 |
| WO | WO 2001/072338 A1 | 10/2001 |
| WO | WO 2002/013786 A2 | 2/2002 |
| WO | WO 2002/087512 A2 | 11/2002 |
| WO | WO 2002/087558 | 11/2002 |
| WO | WO 2002/094254 | 11/2002 |
| WO | WO 2003/004029 A1 | 1/2003 |
| WO | WO 2003/015531 | 2/2003 |
| WO | WO 2003/024430 | 3/2003 |
| WO | WO 2003/026743 | 4/2003 |
| WO | WO 2003/035090 | 5/2003 |
| WO | WO 2003/092676 | 11/2003 |
| WO | WO 2004/004693 A1 | 1/2004 |
| WO | WO 2004/026256 | 1/2004 |
| WO | WO 2004/026283 | 4/2004 |
| WO | WO 2004/037259 | 5/2004 |
| WO | WO 2004/075877 A1 | 9/2004 |
| WO | WO 2005/053587 | 6/2005 |
| WO | WO 2005/123039 A1 | 12/2005 |
| WO | WO 2010/0078486 | 7/2010 |
| WO | WO 2017/222575 A1 | 12/2017 |

OTHER PUBLICATIONS

"Castor oil, hydrogenated," European Pharmacopoeia V.5, p. 1197-1198 (2005).

Declaration by Dr. Alison Fleming, dated Jun. 29, 2007, submitted in U.S. Appl. No. 11/149,867, filed Nov. 2, 2009.

"International Preliminary Report on Patentability," 3 pages, PCT appl. No. PCT/US03/21095 (dated Apr. 25, 2005).

"International Preliminary Report on Patentability," 6 pages, PCT appl. No. PCT/US2005/020588 (dated Oct. 2, 2006).

"International Search Report," 2 pages, PCT appl. No. PCT/US03/21095 (dated Nov. 6, 2003).

"International Search Report," 2 pages, PCT appl. No. PCT/US2016/050092 (dated Nov. 22, 2016).

"International Search Report," 4 pages, PCT appl. No. PCT/US2005/020588 (dated Sep. 9, 2005).

"Supplementary European Search Report," 7 pages, EP appl. No. 03763229.6 (dated Sep. 19, 2008).

Extended European Search Report for European Patent Application No. EP 17188009.9, dated Apr. 10, 2018, 7 pages.

"Written Opinion of the International Searching Authority," 6 pages, PCT appl. No. PCT/US2005/020588 (dated Sep. 9, 2005).

"Written Opinion of the International Searching Authority," 7 pages, PCT appl. No. PCT/US2016/050092 (dated Nov. 22, 2016).

"Written Opinion," 4 pages, PCT appl. No. PCT/US03/21095 (dated Jun. 20, 2004).

Abuse and Mental Health Services Administration, "Results from the 2004 National Survey on Drug Use and Health: National Findings," pp. 1-310 (2005).

Amended Petition for Post Grant Review; PGR2018-00048; U.S. Pat. No. 9,693,961; dated Mar. 28, 2018.

Berkland, et al., "Fabrication of PLG microspheres with precisely controlled and monodisperse size distributions." Journal of Controlled Release (2001); 73(1): 59-74.

Bourret, et al., "Rheological Behaviour of Saturated Polyglycolyzed Glycerides." Journal of Pharmacy and Pharmacology (1994); 46: 538-541.

Breitenbach, J., Melt Extrusion: from Process to Drug Delivery Technology, 54 Eur. J. Pharm. & Biopharm., 107-17 (2002).

Buist et al., "Four salt phases of theophylline," Struct. Chem. Acta Crystal. Sect. C C70:220-224 (2014).

Bush et al., "A comparison of a theophylline-ephedrine combination with terbutaline," Ann. Allergy 41:13-17 (1978) abstract.

Chemical Abstract Society (CAS), Properties for HPMC (CAS reg. No. 9004-65-3) accessed Jun. 29, 2013.

Chemistry: The Central Science, Theodore L. Brown et al, 9th Edition (2003) pp. 492-494.

Choi et al., "Hydrophobic ion pair formation between leuprolide and sodium oleate for sustained release from biodegradable polymeric microspheres," Int. J. Pharm. 203:193-202 (2000).

Choi, et al., "Effect of polymer molecular weight on nanocomminution of poorly soluble drug." Drug Delivery (2008); 15(5): 347-353.

Collegium Pharmaceutical, "Xtampza™ ER (Extended-Release Oxycodone)," FDA Advisory Committee Briefing Document, Sep. 11, 2015, 93 pages.

Detailed Statement of the Factual and Legal Bases for Collegium Pharmaceutical, Inc.'s Paragraph IV Certification With Respect to

(56) References Cited

OTHER PUBLICATIONS

U.S. Pat. Nos. 6,488,963; 7,674,799; 7,674,800; 7,683,072; 7,776,314; 8,114,383; 8,309,060; 8,337,888; 8,808,741; 8,894,987; and 8,894,988dated Feb. 11, 2015.
Detailed Statement of the Factual and Legal Bases for Collegium Pharmaceutical, Inc.'s Paragraph IV Certification With Respect to U.S. Pat. Nos. 7,674,799, 7,674,800, 7,683,072, 7,776,314, 8,309,060, 8,808,741, 8,894,987, 8,894,988, 9,060,976, 9,073,933, 9,492,389, 9,492,391, 9,492,392, 9,492,393, 9,522,919, and 9,675,610dated Aug. 25, 2017.
Collegium's Prelim. Invalidity Contentions in C.A. No. 15-cv-13099-FDS dated Aug. 19, 2016.
Collegium's Prelim. Invalidity Contentions in 15-cv-13099-FDS dated Oct. 5, 2016.
Collegium's Prelim. Invalidity Contentions in 15-cv-13099-FDS dated Jun. 16, 2017.
Collegium's Prelim. Invalidity Contentions in 15-cv-13099-FDS dated Apr. 25, 2017.
Collegium's MOL ISO Motion for Summary Judgment in C.A. No. 15-cv-13099 (FDS) dated Feb. 14, 2017.
Collegium's Reply MOL ISO its Motion for Summary Judgment in C.A. No. 15-cv-13099 (FDS) dated May 12, 2017.
Concerta tablets—Highlights of Prescribing Information, Nov. 2010, 27 pages.
Cortesi, et al., "Sugar cross-linked gelatin for controlled release: microspheres and disks," Biomaterials 19:1641-1649 (1998).
Emås and Nyqvist, "Methods of studying aging and stabilization of spray-congealed solid dispersions with carnauba wax." International Journal of Pharmaceutics (2000); 197(1-2): 117-127, 13 pages.
U.S. Appl. No. 60/376,470 to Ayer et al.
Declaration of Todd Scungio.
Collegium Pharmaceutical Study: Intravenous Abuse Comparison of Oxycodone DETERx™ Versus OxyContin™ (Filed Under Seal).
Complaint, *Purdue Pharma L.P. et al.*, v. *Collegium Pharmaceutical, Inc.*, 17-cv-11814.
Order Granting Consolidation, *Purdue Pharma, L.P. et al.* v. *Collegium Pharmaceutical, Inc.*, 15-cv-13099.
Joint Claim Construction and Prehearing Statement, *Purdue Pharma, L.P. et al.* v. *Collegium Pharmaceutical, Inc.*, 15-cv-13099.
A. Gennaro ed., Remington: The Science and Practice of Pharmacy (20th ed. 2000).
E. Cone et al., "An Iterative Model for in vitro Laboratory Assessment of Tamper Deterrent Formulations", 131 Drug and Alcohol Dependence 100 (2013).
FDA, Abuse-Deterrent Opioids—Evaluation and Labeling: Guidance for Industry (Apr. 2015).
Plaintiffs' Opening Claim Construction Brief, *Purdue Pharma L.P. et al.* v. *Collegium Pharmaceutical, Inc.*, 15-cv-13099 (Redacted version filed in district court).
S. Passik et al., "Psychiatric and Pain Characteristics of Prescription Drug Abusers Entering Drug Rehabilitation", 20:2 J. of Pain & Palliative Care Pharmacotherapy 5 (2006).
Bulletin Technique Gattefossé Report (1988).
S. Harris et al., "Abuse Potential, Pharmacokinetics, Pharmacodynamics, and Safety of Intranasally Administered Crushed Oxycodone HCI Abuse-Deterrent Controlled-Release Tablets in Recreational Opioid Users", 54(4) J. of Clinical Pharmacology 468 (2013).
B. Lara-Hernandez et al., "Effect of Stearic Acid on the Properties of Metronidazole/Methocel K4M Floating Matrices", 45(3) Brazilian J. of Pharm. Scis. 497 (2009).
B. Alberts et al., Essential Cell Biology (2nd ed. 2004).
C. Smith et al., "Oral and Oropharyngeal Perceptions of Fluid Viscosity Across the Age Span", Dysphagia (2006).
Rowe et al. eds., Handbook of Pharmaceutical Excipients (7th ed. 2012).
Y. Zhang et al., "Effect of Processing Methods and Heat Treatment on the Formation of Wax Matrix Tablets for Sustained Drug Release", 6(2) Pharm. Dev. and Tech. 131 (2001).

I. Ghebre-Sellassie ed., Pharmaceutical Pelletization Technology (1989).
Transcript of Conference Call—Aug. 3, 2018.
Non-Addressed PGGs—Exhibit from Deposition of Panayiotis P. Constantinides.
Ratsimbazafy, "Effect of Formulation on the Rheology of Theophylline Compound Suspensions in Gelucires".
Handbook of Pharmaceutical Excipients 3rd Ed. Index.
Handbook of Pharmaceutical Excipients 6th Ed. Index.
Handbook of Pharmaceutical Excipients 6th Ed. Polyoxylglycerides.
McGinity, "Hot-Melt Extrusion as a Pharmaceutical Process".
Purdue Appeal Brief.
Deposition Transcript of Panayiotis P. Constantinides taken on Mar. 20, 2019.
Gennaro, "Remington: The Science and Practice of Pharmacy".
The Pharmaceautical Codex (12th Ed.).
Damian et al, "Physicochemical characterization of solid dispersions of the antiviral agent UC-781 with polyethylene glycol 6000 and Gelucire 44/14".
Hawleys Condensed Chemical Dictionary (13th Ed.).
Krowczynski, "Extended-Release Dosage Forms".
Supplemental Declaration of Dr. Walter G. Chambliss.
Gelucire USPTO Trademark Registration Certificate.
Feb. 2, 2017 Response to Office Action.
Handbook of Pharmaceutical Excipients 3rd Ed. Docusate Sodium, et al.
Declaration of Panayiotis P. Constantinides, Ph.D.
Curriculum Vitae of Panayiotis P. Constantinides (Jun. 2018).
Oxford Dictionary of Science (Alan Isaacs et al. eds., 4th ed. 1999).
'722 application, Apr. 8, 2016 office action.
'722 application, Nov. 2, 2016 office action.
'722 application, May 17, 2017 notice of allowability.
Gattefossé, Oral Route Excipients (2004).
'275 application, Aug. 2, 2017 amendment.
Material safety data sheet for myristic acid (Jul. 6, 2010).
Material safety data sheet for stearic acid (Feb. 24, 2005).
Statement Regarding Suspension of 160 mg OxyContin® Tablets (May 11, 2001).
Knothe et al., A Comprehensive Evaluation of the Melting Points of Fatty Acids and Esters Determined by Differential Scanning Calorimetry, J. Am. Oil Chem. Soc., 86:843-56 (2009).
Constantinides, P.P., Lipid Microemulsions for Improving Drug Dissolution and Oral Absorption: Physical and Biopharmaceutical Aspects, Pharm. Res., 12(11):1561-72 (1995).
Crew M., The Second Quadrant: Analysis of the Historical Use of Solubilization Techs., Drug. Devel. & Delivery, 14(2):22-25 (Mar. 2014).
Orange Book listing for Xtampza 9 mg (last accessed Jul. 3, 2018).
Semjonov, K. et al., The formation and physical stability of two-phase solid dispersion systems of indomethacin in supercooled molten mixtures with different matrix formers, Euro. J. Pharm. Sci. 97:237-46 (2017).
Hearing transcript, *Purdue Pharma L.P.* v. *Collegium Pharmaceuticals, Inc.*, C.A. No. 15-13099-FDS (D. Mass. Jun. 1, 2017).
Handbook of Pharmaceutical Excipients, 6th ed. (2009).
Handbook of Pharmaceutical Excipients, (Ainley Wade & Paul J. Weller eds., 2nd ed. 1994).
S. Hulsmann et al., Melt Extrusion—An Alternative Method for Enhancing the Dissolution Rate of 17β-estradiol Hemihydrate, 49 European Journal of Pharmaceutics and Biopharmaceutics 237-242 (2000).
Manish K. Gupta et al., Hydrogen Bonding With Absorbent During Storage Governs Drug Dissolution From Solid-Dispersion Granules, 19(11) Pharmaceutical Research, 1663-1762 (2002).
Deposition Transcript of Walter G. Chambliss, Ph.D. (Jan. 9, 2019).
Supplemental Declaration of Panayiotis P. Constantinides, Ph.D.
Paul W.S. Heng et al., Role of Surfactant on Drug Release From Tablets, 16(6) Drug Development and Industrial Pharmacy 951-962 (1990).
FDA Guidance for Industry Q1A (R2) Stability Testing of New Drug Substances and Products, Nov. 2003 Revision 2.
FDA's 1996 Inactive Ingredient Guide.

(56) References Cited

OTHER PUBLICATIONS

Gandhi, et al., "Extrusion and spheronization in the development of oral controlled-release dosage forms." Pharmaceutical Science & Technology Today (1999); 2(4): 160-170.
Gennaro, ed., Remington: The Science and Practice of Pharmacology, 20th ed., Lipincott: Baltimore, MD, pp. 704-706 (2000).
Goldberg et al., "Abuse-resistant compositions," U.S. Appl. No. 60/292,809, filed May 23, 2001.
Guidance for Industry Q1A(R2) Stability Testing of New Drug Substances and Products, U.S. Department of Health and Human Services Food and Drug Administration, Center for Drug Evaluation and Research (CDER), Center for Biologics Evaluation and Research (CBER) ("FDA Guidance"), Nov. 2003, ICH, Revision 2, 25 pages.
Handbook of Pharmaceutical Excipients, 2nd ed., (eds. Wade and Weller), American Pharmaceutical Association (1994), pp. 82-83, 325-328, 544-545; 552-553; and 558-561, 16 pages.
Handbook of Pharmaceutical Excipients, (3rd Edition 2000).
Hawley's Condensed Chemical Dictionary, 13th ed., John, Wiley & Sons, Inc., New York, 1997, p. 1178, defining "wax", 4 pages.
Kim and Pack, Microspheres for Drug Delivery, in BioMEMS and Biomedical/Nanotechnology, pp. 19-50, Springer US (2006), 34 pages.
Kraβnig et al., "Optimization of the Synthesis of Oxycodone and 5-Methyloxycodone," Arch. Pharm. Pharm. Med. Chem. 329, 325-326 (1996).
L. Lachman et al., The Theory and Practice of Industrial Pharmacy (3rd ed. 1986).
Lan et al., "Studies on the Synthesis and Thermal Properties of Copoly(L-lactic acid/glycolic acid) by Direct Melt Polycondensation," J. Appl. Polymer Sci. 92:2163-2168 (2004).
Leuner and Dressman, "Improving drug solubility for oral delivery using solid dispersions." European Journal of Pharmaceutics and Biopharmaceutics (2000); 50(1): 47-60.
Material Safety Data Sheet for Myristic Acid (Dec. 11, 1990).
Meyer and Manning, "Hydrophobic Ion Pairing: Altering the Solubility Properties of Biomolecules." Pharmaceutical Research (1998); 15(2): 188-193.
Murthy and Ghebre-Sellassie, "Current perspectives on the dissolution stability of solid oral dosage forms." Journal of Pharmaceutical Sciences (1993); 82(2): 113-126.
National Drug Intelligence Center, "OxyContin Diversion and Abuse" Information Bulletnin, Product No. 2001-L0424-001, Jan. 2001, 6 pages.
Nakamura, et al., "Development of an oral sustained release drug delivery system utilizing pH-dependent swelling of carboxyvinyl polymer", J. Control. Rel., 111:309-315 (2006).
Oxycodone, 11 pages, May 16, 2005, retrieved from: http://www.swgdrug.org/monographs/oxycodone.pdf.
Oxycodone Monograph in the United States Pharmacopeia (2000) ("USP 24") 34 pages.
Oxycontin Label (2001) 22 pages.
Oxycontin Label (2010) 39 pages.
Ozturk et al., "Mechanism of Release from Pellets Coated with an Ethylcellulose-Based Film," J. Control. Rel. 14:203-213 (1990).
Patent Owner's Preliminary Response to Petition for Post-Grant Review; PGR2018-00048; U.S. Pat. No. 9,693,961; dated Jul. 10, 2018.
Patent Owner's Response to Petition for Post-Grant Review; PGR2018-00048; U.S. Pat. No. 9,693,961; dated Jan. 30, 2019.
Petitioner's Reply; PGR2018-00048; U.S. Pat. No. 9,693,961; dated Apr. 12, 2019.
Pöyhia, et al., "The pharmacokinetics and metabolism of oxycodone after intramuscular and oral administration to healthy subjects." British Journal of Clinical Pharmacology (1992); 33(6): 617-621.
Proska, "10-Hydroxythebaine," Arch. Pharm. Pharm. Med. Chem. 332, 369-370 (1999).
Raffin et al., "Sodium pantoprazole-loaded enteric microparticles prepared by spray drying: Effect of the scale of production and process validation," Int. J. Pharm. 324:10-18 (2006).
Ramanathan et al., "Dihydrocodeine, Dihydrocodeinone, 14-Hydroxydihydrocodeinone & Their Derivatives," Indian Jour. of Technology, vol. 2, No. 10, 350-351 (1964).
Redden et al., "In vitro hydrolysis of polyunsaturated fatty acid N-acyloxymethyl derivatives of theophylline," Int. J. Pharm. 165:87-96 (1998).
Remington, The Science and Practice of Pharmacy (19th Edition 1995) p. 206.
Rodriguez et al., "Description and preliminary evaluation of a new ultrasonic atomizer for spray-congealing processes," Int. J. Pharm. 183(2):133-143 (1999).
Sjökvist, et al., "Physicochemical aspects of drug release. XIV. The effects of some ionic and non-ionic surfactants on properties of a sparingly soluble drug in solid dispersions." International Journal of Pharmaceutics (1992); 79(1-3): 123-133.
Spansule® Capsule Technology, 2013, 11 pages.
J. Sprowls, Ph.D., Prescription Pharmacy (2nd Ed. 1970).
Takka et al., "Effect of anionic polymers on the release of propanol hydrochloride from matrix tablets," Eur. J. Pharm. Biopharm. 52:75-82 (2001).
Teva's Amended Preliminary Invalidity Contentions in C.A. No. 18-300-LPS-CJB dated Dec. 21, 2018.
Detailed Factual and Legal Bases for Teva Pharmaceuticals USA's Paragraph IV Certification that the Claims of U.S. Pat. Nos. 7,399,488; 7,771,707; 8,449,909; 8,557,291; 8,758,813; 8,840,928; 9,044,398; 9,248,195; 9,592,200; 9,682,075; 9,737,530; and, 9,763,883 Are Invalid, Unenforceable and/or Not Infringed dated Jan. 9, 2018.
Detailed Factual and Legal Bases for Teva Pharmaceuticals USA's Paragraph IV Certification That the Claims of U.S. Pat. No. 9,968,598 Are Invalid, Unenforceable and/or Not Infringed dated Oct. 18, 2018.
Detailed Factual and Legal Bases for Teva Pharmaceuticals USA's Paragraph IV Certification That the Claims of U.S. Pat. No. 10,004,729 Are Invalid, Unenforceable and/or Not Infringed dated Oct. 18, 2018.
Detailed Factual and Legal Bases for Teva Pharmaceuticals USA's Paragraph IV Certification That the Claims of U.S. Pat. No. 10,004,729 Are Invalid, Unenforceable and/or Not Infringed dated Mar. 27, 2019.
Teva's Preliminary Invalidity Contentions for Consolidated Patents-in-Suit in C.A. No. 18-300-LPS-CJB dated Feb. 8, 2019.
Toxicological Evaluation of Some Food Colours, Emulsifiers, Stabilizers, Anti-Caking Agents and Certain Other Substances FAO Nutrition Meetings Report Series No. 46A WHO/FOOD ADD/70. 36, Report on Deliberations of the Joint FAO/WHO Expert Committee on Food Additives, Rome, May 27-Jun. 4, 1969 ("FAO/WHO report"), 162 pages.
Weiss, "Derivatives of Morphine. II. Demethylation of 14-hydroxycodeinone. 14-Hydroxymorphinone and 8,14-Dihydroxydihydromorphinone," J. Org. Chem., 1957, 22 (11), pp. 1505-1508.
World Health Organization, "Specifications for the Identity and Purity of Food Additives and Their Toxicological Evaluation," World Health Organization Technical Report Series No. 445, FAO Nutrition Meetings Report Series No. 46, Jun. 1969, 43 pages.
U.S. Department of Health and Human Services et al., "Abuse-Deterrent Opioids—Evaluation and Labeling. Guidance for Industry," http://www.fda.gov/Drugs/GuidanceComplianceRegulatoryInformation/Guidances/default.htm, 29 pages. (Apr. 2015).
U.S. Department of Health and Human Services et al., "Guidance for Industry Q1A(R2) Stability Testing of New Drug Substances and Products," Nov. 2003, Revision 2, 25 pages, retrieved from: https://www.fda.gov/downloads/drugs/guidances/ucm073369.pdf.
U.S. Appl. No. 60/287,509, "Pharmaceutical composition which reduces or eliminates drug abuse potential," Joshi et al., 15 pages, filed Apr. 30, 2001.
U.S. Appl. No. 60/288,211, "Once-a-day oxycodone formulations," Oshlack et al., 43 pages, filed May 2, 2001.
U.S. Appl. No. 60/393,876, "Abuse-resistant formulations of OxyContin and other drugs," Klibanov et al., 35 pages, filed Jul. 5, 2002.
U.S. Appl. No. 60/579,191, "Abuse-deterrent drug formulations," Fleming et al., 35 pages, filed Jun. 12, 2004.

(56) References Cited

OTHER PUBLICATIONS

Yow et al., "Combined Streptomycin and Erythromycin Therapy in Subacute Bacterial Endocarditis." Am. J. Med. (1954); 16(4):613.
Zhang, "Hot-Melt Extrusion As a Novel Technology to Prepare Sustained-Release Dosage Forms," Dissertation, University of Texas at Austin, Dec. 1999, 286 pages.
Ansel, Howard C., et al., "Pharmaceutical Dosage Forms and Drug Delivery Systems," 7th Edition, 1999, pp. 1-2, 23-163, 179-243, 397-449, 552-562, Lippincott Williams & Wilkins, United States.
Aulton, Michael E. (ed.), "Pharmaceutics, The Science of Dosage Form Design," Reprinted 2000, pp. 1-2, 17-37, 62-80, 131-211, 304-321, 359-380, 550-677, Churchill Livingston, China.
Banker, Gilbert S. (ed.) et al., "Modern Pharmaceutics," Third Edition, Revised and Expanded, Drugs and the Pharmaceutical Sciences, vol. 72, 1996, pp. 21-73, 75-119, 121-153, 155-178, 333-394, 441-487, 575-609, 727-772, Marcel Dekker, Inc., United States.
Bodmeier, R., et al., "Process and Formulation Variables in the Preparation of Wax Microparticles by a Melt Dispersion Technique. I. Oil-in-water technique for water-insoluble drugs," Journal of Microencapsulation, 1992, vol. 9, No. 1, pp. 89-98.
Gennaro, Alfonso (ed.), "Remington: The Science and Practice of Pharmacy," 20th Edition, 2000, pp. 1-3, 335-355, 654-666, 669-752, 780-820, 858-929, 995-1004, 1098-1155, 1175-1182, 1395-1399, 2037-2038, Lippincott Williams & Wilkins, Baltimore, MD, United States.
Hillery, Anya M. (ed.) et al., "Drug Delivery: Fundamentals & Applications," 2017, Second Edition, Section 1.3, pp. 3-4, CRC Press, Taylor & Francis Group, United States.
Hillery, Anya M. (ed.) et al., "Drug Delivery and Targeting for Pharmacists and Pharmaceutical Scientists," 2001, Section 1, Chapter 1, pp. 1-48, Taylor & Francis, United States.
Pursuant to 37 C.F.R. §1.98, copies of non-US patent documents, Cite Nos. 193, 196, 206, 221, 233, 236, 240, 243-252, 255-318, 321, 323, 327, 328, 331, 334, 336-339, 341-343, 345, 347, 349, 352, 353, 355-360, 362, 363, and 365-369, and 371.
No copies of the publications listed on the attached Form used in lieu of PTO/SB/08 entitled Information Disclosure Statement by Applicant, except for the Cite Nos. referred to above, are being provided pursuant to 37 C.F.R. §1.98(d) because the publications were previously cited by or submitted to the Office in prior U.S. Appl. No. 15/950,656 (U.S. Pat. No. 10,188,644), U.S. Appl. No. 15/649,024 (U.S. Pat. No. 9,968,598) and U.S. Appl. No. 15/255,859 (U.S. Pat. No. 9,737,530) to which the above-identified application claims priority under 35 U.S.C. §120.
U.S. Appl. No. 10/614,866 (U.S. Pat. No. 7,399,488).
U.S. Appl. No. 11/149,867 (U.S. Pat. No. 7,771,707).
U.S. Appl. No. 12/473,073 (U.S. Pat. No. 8,557,291).
U.S. Appl. No. 12/823,628 (U.S. Pat. No. 8,449,909).
U.S. Appl. No. 12/965,572 (U.S. Pat. No. 8,840,928).
U.S. Appl. No. 13/551,455 (U.S. Pat. No. 9,044,398).
U.S. Appl. No. 13/870,690 (U.S. Pat. No. 8,758,813).
U.S. Appl. No. 14/054,513 (U.S. Pat. No. 9,248,195).
U.S. Appl. No. 14/147,088 (U.S. Pat. No. 9,763,883).
U.S. Appl. No. 14/320,086 (U.S. Pat. No. 9,682,075).
U.S. Appl. No. 14/946,275 (U.S. Pat. No. 9,592,200).
U.S. Appl. No. 15/255,859 (U.S. Pat. No. 9,737,530).
U.S. Appl. No. 15/606,112 (U.S. Pat. No. 10,004,729).
U.S. Appl. No. 15/649,024 (U.S. Pat. No. 9,968,598).
U.S. Appl. No. 15/950,656 (U.S. Pat. No. 10,188,644).
U.S. Appl. No. 15/681,589.
U.S. Appl. No. 15/725,818.
U.S. Appl. No. 15/727,134.
U.S. Appl. No. 15/699,229.
U.S. Appl. No. 16/017,097.
U.S. Appl. No. 16/017,099, and.
U.S. Appl. No. 16/243,557.
Berge et al., "Pharmaceutical Salts," J. Pharma Sci, Jan. 1977, 66(1):1-19.
Gould, "Salt selection for basic drugs,", Int J Pharma, 33 (1986) 201-217.
USP Official Monographs, "Erythromycin Stearate" and "Erythromycin Stearate Tablets," 2000, pp. 675 and 676.
Apicella, A., "Poly(ethylene oxide)(PEO) and Different Molecular Weight PEO Blends Monolithic Devices for Drug Release," Biomaterials, vol. 14, No. 2, 1993, pp. 83-90.
Apicella, et al. "Poly(ethylene oxide)(PEO) Constant Release Monolithic Devices," Polymers in Medicine: Biomedical and Pharmaceutical Applications, Chapter 3 (1992), pp. 23-37.
Apicella, et al., "Poly(ethylene oxide)-Based Delivery Systems," Polymeric Drugs and Drug Administration, ACS Symposium Series 545, Chapter 9 (1994), pp. 111-125.
Audebrand et al. Gelation of pectin-alginate mixture: ultrastructure and rheological properties. 3'u International Symposium on Food Rheology and Structure. 2003, Zurich, Switzerland. Proceedings: 517-518.
Bettini, et al., "Translocation of drug particles in HPMC matrix gel layer: effect of drug solubility and influence on release rate," Journal of Controlled Release, vol. 70, No. 3, Feb. 2001, pp. 383-391.
Bhatia, R., "Effect of Molecular Mass, Concentration and Temperature on the Rheological Properties of Non-Newtonian Aqueous Polymeric Solutions," 114, 2011, 202 pqs.
Chien, View., et al., "Syringeability of Nonaqueous Parenteral Formulations—Development and Evaluation of Testing Apparatus," Journal of Parenteral Science and Technology, vol. 35, No. 6, Nov. 1981, pp. 281-284.
*CRC Handbook of Chemistry and Physics*, p. F-56 (59th ed. 1978), 3 pages.
Decision to Institute Trial for Inter Partes Review, IPR2016-01027 of U.S. Pat. No. 9,060,976, dated Nov. 9, 2016, 32 pages.
Decision to Institute Trial for Inter Partes Review, IPR2016-01028 of U.S. Pat. No. 9,060,976, dated Nov. 9, 2016, 40 pages.
Decision to Institute Trial for Inter Partes Review, IPR2016-01412 of U.S. Pat. No. 9,034,376, dated Feb. 14, 2017, 25 pages.
Decision to Institute Trial for Inter Partes Review, IPR2016-01413 of U.S. Pat. No. 9,034,376, dated Jan. 18, 2017, 25 pages.
Declaration of Dr. Anthony Palmieri for IPR2016-01412, dated Jul. 15, 2016, 67 pages.
Declaration of Dr. Anthony Palmieri for IPR2016-01413, dated Jul. 15, 2016, 56 pages.
Deighan, C.J., et al., "Ehabdomyolysis and Acute Renal Failure Resulting From Alcohol and Drug Abuse," OJ Med., vol. 93, 2000, oas. 29-33.
Dexter, M.B., et al., "The Evaluation of the Force to Expel Oily Injection Vehicles from Syringes," J. Pharm. Pharmacol., vol. 31, Aug. 1979, The Pharmaceutical Society of Great Britain, pp. 497-500.
Exhibit 1001 of IPR2016-00849, Dated Apr. 6, 2016: U.S. Pat. No. 8,389,007, 24 pages.
Exhibit 1001 of IPR2016-01027 and IPR2016-01028, dated May 11, 2016: U.S. Pat. No. 9,060,976 (The '976 Patent), 24 pages.
Exhibit 1002 of IPR2016-00849, Dated Apr. 6, 2016: Expert Declaration of Arthur H. Kibbe (Dated Apr. 6, 2016), 140 pages.
Exhibit 1002 of IPR2016-01027 and IPR2016-01028, dated May 11, 2016: U.S. Pat. No. 8,337,888 (The '888 Patent), 25 pages.
Exhibit 1003 of IPR2016-00849, Dated Apr. 6, 2016: U.S. Pat. No. 8,337,888, 25 pages.
Exhibit 1003 of IPR2016-01027 and IPR2016-01028, dated May 11, 2016: *Purdue Pharma L.P. et al.* v. *Amneal Pharmaceuticals LLC*, No. 13-cv-3372-SHS (S.D.N.Y. Apr. 8, 2015) Findings of Facts and Conclusion of Law ("SONY Decision"), 69 pages.
Exhibit 1004 of IPR2016-00849, Dated Apr. 6, 2016: *Purdue Pharma LP., et. al.* v. *Amneal Pharmaceuticals, LLC*, No. 13-cv-3372 (SHS) (S.D.N.Y. Apr. 8, 2015) (Findings of Fact and Conclusions of Law), 69 pages.
Exhibit 1004 of IPR2016-01027 and IPR2016-01028, dated May 11, 2016: *Purdue Pharma L.P. et al.* v. *Amneal Pharmaceuticals LLC*, No. 2015-1654 (Fed. Cir. Apr. 8, 2016) Order ("Federal Circuit Decision"), 2 pages.
Exhibit 1005 of IPR2016-00849, Dated Apr. 6, 2016: *Physicians' Desk Reference*, 54th Edition (2000), 15 pages.

(56) References Cited

OTHER PUBLICATIONS

Exhibit 1005 of IPR2016-01027 and IPR2016-01028, dated May 11, 2016: U.S. Pat. No. 8,101,630 ("Kumar Patent"). 21 pages.
Exhibit 1006 of IPR2016-00849, Dated Apr. 6, 2016: U.S. Patent Publication No. 2002/0187192, 6 pages.
Exhibit 1006 of IPR2016-01027 and IPR2016-01028, dated May 11, 2016: U.S. Patent Publication No. 2010/0216829 ("Kumar Publication"), 23 pages.
Exhibit 1007 of IPR2016-00849, Dated Apr. 6, 2016: U.S. Appl. No. 60/287,509, filed Apr. 30, 2001, 15 pages.
Exhibit 1007 of IPR2016-01027 and IPR2016-01028, dated May 11, 2016: Complaint, *Purdue Pharma LP. et al. v. Amneal Pharmaceuticals LLC*, 15-cv-831, filed Sep. 17, 2015, 9 pages.
Exhibit 1008 of IPR2016-00849, Dated Apr. 6, 2016: U.S. Patent Publication No. 2003/0064122, 7 pages.
Exhibit 1008 of IPR2016-01027 and IPR2016-01028, dated May 11, 2016: Complaint, *Purdue Pharma LP. et al. v. Amneal Pharmaceuticals LLC*, 15-cv-1152, filed Dec. 15, 2015, 36 pages.
Exhibit 1009 of IPR2016-00849, Dated Apr. 6, 2016: U.S. Appl. No. 60/292,809, filed May 23, 2001, 12 pages.
Exhibit 1009 of IPR2016-01027, dated May 11, 2016: Declaration of Dr. Anthony Palmieri ("Palmieri Declaration"), 43 pages.
Exhibit 1009 of IPR2016-01028, dated May 11, 2016: Declaration of Dr. Anthony Palmieri ("Palmieri Declaration"), 45 pages.
Exhibit 1011 of IPR2016-00849, Dated Apr. 6, 2016: U.S. Pat. No. 3,980,766, 5 pages.
Exhibit 1011 of IPR2016-01027 and IPR2016-01028, dated May 11, 2016: International Patent Publication No. WO 99/32120 ("Palermo"), 47 pages.
Exhibit 1012 of IPR2016-00849, Dated Apr. 6, 2016: U.S. Pat. No. 4,070,494, 6 pages.
Exhibit 1012 of IPR2016-01027 and IPR2016-01028, dated May 11, 2016: *The Handbook of Pharmaceutical Excipients* 399-400, 655 (3rd ed. 2000), 5 pages.
Exhibit 1013 of IPR2016-00849, Dated Apr. 6, 2016: U.S. Pat. No. 8,337,888 Prosecution File History (Notice of Allowance, dated Dec. 3, 2012), 6 pages.
Exhibit 1013 of IPR2016-01027 and IPR2016-01028, dated May 11, 2016: International Patent Publication No. WO 97/49384 ("McGinity"), 29 pages.
Exhibit 1014 of IPR2016-00849, Dated Apr. 6, 2016: U.S. Appl. No. 60/310,534, filed Aug. 6, 2001, 67 pages.
Exhibit 1014 of IPR2016-01027 and IPR2016-01028, dated May 11, 2016: U.S. Patent Publication No. 2002/0187192 ("Joshi"), 6 pages.
Exhibit 1015 of IPR2016-00849, Dated Apr. 6, 2016: Brief of Plaintiffs-Appellant, *Purdue Pharma LP., et. al. v. Amneal Pharmaceuticals, LLC*, No. 15-1654 (Fed. Cir. Aug. 12, 2015), 198 pages.
Exhibit 1015 of IPR2016-01027 and IPR2016-01028, dated May 11, 2016: International Patent Publication No. WO 95/20947 ("Bastin"), 39 pages.
Exhibit 1016 of IPR2016-00849, Dated Apr. 6, 2016: Reply Brief of Plaintiffs-Appellant, *Purdue Pharma LP., et. al. v. Amneal Pharmaceuticals, LLC*, No. 15-1654 (Fed. Cir. Dec. 23, 2015), 41 pages.
Exhibit 1016 of IPR2016-01027 and IPR2016-01028, dated May 11, 2016: OxyContin, *Physicians' Desk Reference* 2569-74 (53rd ed. 1999), 8 pages.
Exhibit 1017 of IPR2016-00849, Dated Apr. 6, 2016: Meier, "U.S. Asks Painkiller Maker to Help Curb Wide Abuse" NY Times (May 1, 2001), 3 pages.
Exhibit 1017 of IPR2016-01027 and IPR2016-01028, dated May 11, 2016: *Purdue Pharma LP. et al. v. Amneal Pharmaceuticals LLC*, No. 2014-1306, -1307 (Fed. Cir. Feb. 1, 2016), 27 pages.
Exhibit 1018 of IPR2016-00849, Dated Apr. 6, 2016: Department of Justice, *Information Bulletin: OxyContin Diversion and Abuse* (Jan. 2001), 6 pages.
Exhibit 1018 of IPR2016-01027 and IPR2016-01028, dated May 11, 2016: Department of Justice, *Information Bulletin: OxyContin Diversion and Abuse* (Jan. 2001), 6 pages.

Exhibit 1019 of IPR2016-00849, Dated Apr. 6, 2016: U.S. Pat. No. 6,309,663, 55 pages.
Exhibit 1019 of IPR2016-01027 and IPR2016-01028, dated May 11, 2016: Barry Meier, *U.S. Asks Painkiller Maker to Help Curb Wide Abuse*, The New York Times (Mav 1, 2001), 3 pages.
Exhibit 1010 of IPR2016-00849, Dated Apr. 6, 2016: U.S. Pat. No. 5,183,654, 6 pages.
Exhibit 1010 of IPR2016-01027 and IPR2016-01028, dated May 11, 2016: *Curriculum Vitae* of Anthony Palmieri, Ph.D., 13 pages.
Exhibit 1020 of IPR2016-00849, Dated Apr. 6, 2016: International Patent Publication No. WO 99/44591, 57 pages.
Exhibit 1020 of IPR2016-01027 and IPR2016-01028, dated May 11, 2016: Brief of Plaintiffs-Appellants in *Purdue Pharma LP. et al. v. Amneal Pharmaceuticals LLC*, No. 2015-1654 (Fed. Cir. Aug. 12, 2015), 198 pages.
Exhibit 1021 of IPR2016-00849, Dated Apr. 6, 2016: U.S. Pat. No. 4,710,384, 6 pages.
Exhibit 1021 of IPR2016-01027 and IPR2016-01028, dated May 11, 2016: Reply Brief of Plaintiffs-Appellants in *Purdue Pharma LP. et al. v. Amneal Pharmaceuticals LLC*, No. 2015-1654 (Fed. Cir. Dec. 23, 2015), 41 pages.
Exhibit 1022 of IPR2016-00849, Dated Apr. 6, 2016: U.S. Patent Publication No. 2002/0142039, 9 pages.
Exhibit 1022 of IPR2016-01027 and IPR2016-01028, dated May 11, 2016: U.S. Appl. No. 13/726,324, Originally Filed Specification, filed Dec. 24, 2012, 62 pages.
Exhibit 1023 of IPR2016-00849, Dated Apr. 6, 2016: Banker, Modern Pharmaceutics, 3rd Edition (1996), 66 pages.
Exhibit 1023 of IPR2016-01027 and IPR2016-01028, dated May 11, 2016: U.S. Appl. No. 13/349,449, Originally Filed Specification, filed Jan. 12, 2012, 62 pages.
Exhibit 1024 of IPR2016-00849, Dated Apr. 6, 2016: Kibbe, Handbook of Pharmaceutical Excipients, 3rd Edition (2000), 18 pages.
Exhibit 1024 of IPR2016-01027 and IPR2016-01028, dated May 11, 2016: U.S. Appl. No. 12/653,115, Originally Filed Specification, filed Dec. 8, 2009, 62 pages.
Exhibit 1025 of IPR2016-00849, Dated Apr. 6, 2016: U.S. Pat. No. 5,422,134, 11 pages.
Exhibit 1025 of IPR2016-01027 and IPR2016-01028, dated May 11, 2016: U.S. Appl. No. 10/214,412, Originally Filed Specification, filed Aug. 6, 2002, 62 pages.
Exhibit 1026 of IPR2016-00849, Dated Apr. 6, 2016: European Patent Publication No. EP 0974345 A2, 4 pages.
Exhibit 1026 of IPR2016-01027 and IPR2016-01028, dated May 11, 2016: U.S. Appl. No. 60/310,534, 64 pages.
Exhibit 1027 of IPR2016-00849, Dated Apr. 6, 2016: Waugh, et. al., *Peroperative venography to ensure accurate sapheno-popiteal vein ligation*, British Medical Journal (Jun. 28, 1980), 2 pages.
Exhibit 1028 of IPR2016-00849, Dated Apr. 6, 2016: Abdala, et al., Can HIV-1-Contaminated Syringes Be Disinfected?, Journal of Acquired Immune Deficiency Syndromes 28:487-494 (2001), 8 pages.
Exhibit 1028 of IPR2016-01027 and IPR2016-01028, dated May 11, 2016: U.S. Appl. No. 13/726,324, Preliminary Amendment, filed Dec. 24, 2012, 8 cases.
Exhibit 1029 of IPR2016-00849, Dated Apr. 6, 2016: Needle, et al., *HIV Risk Behaviors Associated with the Injection Process: Multiperson Use of Drug Injection Equipment and Paraphernalia in injection Drug User Networks*, Substance and Misuse 33:2401-2423 (1998), 22 pages.
Exhibit 1029 of IPR2016-01027 and IPR2016-01028, dated May 11, 2016: U.S. Appl. No. 13/726,324, Supplemental Amendment, filed Jan. 23, 2013, 10 pages.
Exhibit 1030 of IPR2016-00849, Dated Apr. 6, 2016: Neilloud, et al., Pharmaceutical Emulsions and Suspensions (2000), 29 pages.
Exhibit 1030 of IPR2016-01027 and IPR2016-01028, dated May 11, 2016: U.S. Appl. No. 13/726,324, Office Action, dated Jul. 15, 2013, 10 pages.
Exhibit 1031 of IPR2016-00849, Dated Apr. 6, 2016: European Patent No. EP 0828802 81, 17 pages.

(56) References Cited

OTHER PUBLICATIONS

Exhibit 1031 of IPR2016-01027 and IPR2016-01028, dated May 11, 2016: U.S. Appl. No. 13/726,324, Amendment and Response, dated Jan. 15, 2014, 27 pages.
Exhibit 1032 of IPR2016-00849, Dated Apr. 6, 2016: Buhler, Kollidon: Polyvinylpyrrolidone for the pharmaceutical industry, 4th Edition (1998), 288 pages.
Exhibit 1032 of IPR2016-01027 and IPR2016-01028, dated May 11, 2016: U.S. Appl. No. 13/726,324, Notice of Allowance, dated Oct. 31, 2014, 8 pages.
Exhibit 1033 of IPR2016-00849, Dated Apr. 6, 2016: U.S. Pat. No. 4,737,151, 6 pages.
Exhibit 1033 of IPR2016-01027 and IPR2016-01028, dated May 11, 2016: U.S. Appl. No. 13/726,324, Request for Continued Examination, filed Jan. 5, 2015, 3 pages.
Exhibit 1034 of IPR2016-00849, Dated Apr. 6, 2016: Chien, et al., Syringeability of Nonaqueous Parenteral Formulations-Development and Evaluation of a Testing Apparatus, PDA Journal of Science and Technology 35:281-284 (1981), 6 pages.
Exhibit 1034 of IPR2016-01027 and IPR2016-01028, dated May 11, 2016: U.S. Appl. No. 13/726,324, Communication from Applicant, dated Jan. 29, 2015, 1 page.
Exhibit 1035 of IPR2016-00849, Dated Apr. 6, 2016: Budavari, et al., The Merck Index, 12th Edition 1996, 4 pages.
Exhibit 1035 of IPR2016-01027 and IPR2016-01028, dated May 11, 2016: U.S. Appl. No. 13/726,324, Information Disclosure Statement, filed Apr. 14, 2015, 8 pages.
Exhibit 1036 of IPR2016-00849, Dated Apr. 6, 2016: Maggi, et. al., High molecular weight polyethylene oxides (PEOs) as an alternative to HPMC in controlled release dosage forms, International Journal of Pharmaceutics 195:229-238 (2000), 10 pages.
Exhibit 1036 of IPR2016-01027 and IPR2016-01028, dated May 11, 2016: U.S. Appl. No. 13/726,324, Notice of Allowance, dated May 12, 2015, 9 pages.
Exhibit 1037 of IPR2016-00849, Dated Apr. 6, 2016: The United States Pharmacopeia (2000), 10 pages.
Exhibit 1037 of IPR2016-01027 and IPR2016-01028, dated May 11, 2016: U.S. Pat. No. 4,861,598 ("Oshlack"), 5 pages.
Exhibit 1038 of IPR2016-00849, Dated Apr. 6, 2016: Mark, et. al., Encyclopedia of Polymer Science and Engineering (1986), 100 pages.
Exhibit 1038 of IPR2016-01027 and IPR2016-01028, dated May 11, 2016: U.S. Appl. No. 60/287,509 ("Joshi Provisional"), 14 pages.
Exhibit 1039 of IPR2016-00849, Dated Apr. 6, 2016: Poll, *The Story of the Gauge*, Anaesthesia, 54:575-581 (1999), 7 pages.
Exhibit 1039 of IPR2016-01027 and IPR2016-01028, dated May 11, 2016: Oral Dosage Forms, II (94) Remington: The Science and Practice of Pharmacy 1666-69 (19th ed. 1995), 9 pages.
Exhibit 1040 of IPR2016-00849, Dated Apr. 6, 2016: Bellingham, *A reference guide to insulin pens*, The Pharmaceutical Journal (Jun. 10, 2000), 3 pages.
Exhibit 1041 of IPR2016-00849, Dated Apr. 6, 2016: *Purdue Pharma L.P. et al. v. Acura Pharmaceuticals, Inc., et. al.*, 15-cv-00292-RGA (D. Del). (Egalet Proof of Service), 2 pages.
Exhibit 1042 of IPR2016-00849, Dated Apr. 6, 2016: *Purdue Pharma L.P. et al. v. Acura Pharmaceuticals, Inc., et. al.*, 15-cv-00292-RGA (D. Del). (Acura Proof of Service), 1 page.
Exhibit 1043 of IPR2016-00849, Dated Apr. 6, 2016: *Purdue Pharma LP., et. al. v. Amneal Pharmaceuticals, LLC*, No. 13-cv-3372 (SHS) (Trial Transcript on Jul. 14, 2014), 198 pages.
Exhibit 1044 of IPR2016-00849, Dated Apr. 6, 2016: Bailey, et. al., *High Molecular Weight Polymers of Ethylene Oxide*, Industrial and Engineering Chemistry 50:8-11 (1958), 4 pages.
Exhibit 1045 of IPR2016-00849, Dated Apr. 6, 2016: Gard, FDA advisers side against Purdue's new painkiller, citina dosina danaers, FierceBiotech (Sep. 11, 2015), 2 pages.
Exhibit 1046 of IPR2016-00849, Dated Apr. 6, 2016: International Patent Publication No. WO 96/06528, 66 pages.
Exhibit 1047 of IPR2016-00849, Dated Apr. 6, 2016: International Patent Publication No. WO 95/18602, 29 pages.
Exhibit 1048 of IPR2016-00849, Dated Apr. 6, 2016: Markus, et. al., *Microscopic air embolism during cerebral angiography and strategies for its avoidance*, The Lancet 341:784-87 (1993), 4 pages.
Exhibit 1049 of IPR2016-00849, Dated Apr. 6, 2016: U.S. Pat. No. 6,096,722, 85 pages.
Exhibit 1050 of IPR2016-00849, Dated Apr. 6, 2016: Singh, et. al., *Transdermal iontophoretic delivery of methylphenidate HG/* in vitro, International Journal of Pharmaceutics 178: 121-128 (1999), 8 pages.
Exhibit 1051 of IPR2016-00849, Dated Apr. 6, 2016: Webster's Third New International Dictionary (1986), 3 pages.
Exhibit 1052 of IPR2016-00849, Dated Apr. 6, 2016: Henderson's Dictionary of Biological Terms 10th Edition (1989), 3 pages.
Exhibit 1053 of IPR2016-00849, Dated Apr. 6, 2016: Apicella, et. al., Poly(ethylene oxide) (PEO) and different molecular weight PEO blends monolithic devices for drug release, Biomaterials 14:83-90 (1993), 9 pages.
Expert Declaration of Dr. Eric M. Gaier for IPR2016-01027 of U.S. Pat. No. 9,060,976, dated Aug. 12, 2016, 63 pages.
Expert Declaration of Dr. Eric M. Gaier for IPR2016-01028 of U.S. Pat. No. 9,060,976, dated Aug. 12, 2016, 63 pages.
Expert Declaration of Dr. Stephen Byrn for IPR2016-01027 of U.S. Pat. No. 9,060,976, dated Aug. 12, 2016, 116 pages.
Expert Declaration of Dr. Stephen Byrn for IPR2016-01028 of U.S. Pat. No. 9,060,976, dated Aug. 12, 2016, 113 pages.
Expert Declaration of Dr. Stephen Byrn for IPR2016-01412 of U.S. Pat. No. 9,034,376, dated Nov. 18, 2016, 96 pages.
Expert Declaration of Dr. Stephen Byrn for IPR2016-01413 of U.S. Pat. No. 9,034,376, dated Oct. 21, 2016, 94 pages.
Findings of Fact and Conclusions of Law, in re: Oxycontin Antitrust Litigation, Case 1:04-md-01603-SHS, Apr. 8, 2015, pp. 1-69.
Handbook of Pharmaceutical Excipients, 1986, pp. 234-239, American Pharmaceutical Association, Washington D.C., United States.
*Handbook of Pharmaceutical Excipients*, pp. 252-255, 399-400, 655 (3rd ed. 2000), 9 pages.
Hardman, Joel G., et al., Goodman & Gilman's the Pharmacological Basis of Therapeutics, 9th Edition, 1996, pp. 3-27, 521-555, 557-577, McGraw-Hill, United States.
Hem, Stanley, et al., "Tissue Irritation Evaluation of Potential Parenteral Vehicles," Drug Development Communications, 1:5, 1974, pp. 471-477, Marcel Dekker, Inc.
Heng, Paul, et al., "Role of Surfactant on Drug Release from Tablets", Drug Development and Industrial Pharmacy, Oct. 20, 2008, pp. 951-962, Taylor & Francis, London, United Kingdom.
Huang, H., et al., "Preparation of Controlled Release Oral Dosage Forms by Low Temperature Melt Extrusion," The AAPS Journal, AAPS PharmaSci, 2000, 2(S1), 3 pages.
Industrial and Engineering Chemistry I/EC, Golden Anniversary Year 50, Pattern for Progress, vol. 50, No. 1, Jan. 10, 1958, pp. 8-11, American Chemical Society, Easton, PA, United States.
Kalant, H., et al., "Death in Amphetamine Users: Causes and Rates," CMA Journal, vol. 112, Feb. 8, 1975, pp. 299-304.
Kibbe, Arthur, H., "Polyethylene Oxide," Handbook of Pharmaceutical Excipients, Third Edition, 2000, pp. 399-400, PhP Pharmaceutical Press, London, United Kingdom.
Kim, C., "Drug Release from Compressed Hydrophilic POLYOX-WSR Tablets," Journal of Pharmaceutical Sciences, vol. 84, No. 3, Mar. 1995, pp. 303-306.
Levy et al. The effect of certain additives on the gel point of methylcellulose. J. Am. Pharm. Assoc. Am. Pharm. Assoc., 1958, 47(1):44-46.
Maggi, L., et al, "Dissolution Behaviour of Hydrophilic Matrix Tablets Containing Two Different Polyethylene Oxides (PEOs) for the Controlled Release of a Water-Soluble Drug," Biomaterials, vol. 23, oas. 1113-1119 (2002).
Masuda et al. Swelling of poly(ethylene oxide) gel in aqueous solutions of sodium dodecyl sulfate with added sodium chloride, Colloid. and Polymer Science, 2002, 280(5):490-494.
Medical Economics Company, Inc., The 1997 Physician's Desk Reference ("PDR") entry for Oxycontin®, 51st edition, Nov. 1996, Montvale, NJ pp. 2163-2164.

(56) References Cited

OTHER PUBLICATIONS

Meier, Barry, "U.S. Asks Painkiller Maker to Help Curb Wide Abuse," The New York Times, May 1, 2001, 3 pgs.
Meunier, *Multicomponent Biopolymer Gels: The Agarose-Carrageenan-Gellan System*, 3rd International Symposium on Food Rheology and Structure, 2003, Zurich, Switzerland, Proceedings: 493-494.
Moroni, et al., "Application of Poly(oxyethylene) Homopolymers in Sustained Release Solid Formulation," Drug Dev. and Indus. Pharmacy, 21(12), pp. 1411-1428 (1995).
Opinion & Order filed May 27, 2014, Case 1:04-md-01603-SHS, 24 pgs.
*Opioid bill passes, but there's little money to act on its wish list, Politics & Government* (Jul. 13, 2016), available at http://www.newsoberver.com/news/politics-government/article89403007.html (last visited Jul. 14, 2016), 5 pages.
Order, *In re Oxycontin Litigation*, Case15-1654, Document 78, pp. 1-2, (CAFC Apr. 8, 2016).
Ortho-McNeil-Janssen Pharmaceuticals, Inc. (2010). Prescribing Information for Concerta Extended-Release Tablets, 27 pqs.
Paragraph IV Patent Certification Notice for Amendment to ANDA 202762 (2011).
Paragraph IV Patent Certification Notice for ANDA 202352 (2013).
Paragraph IV Patent Certification Notice for ANDA 202372 (2011).
Paragraph IV Patent Certification Notice for ANDA 202372 (2013).
Paragraph IV Patent Certification Notice for ANDA 202434 (2011).
Paragraph IV Patent Certification Notice for ANDA 202434 (2013).
Paragraph IV Patent Certification Notice for ANDA 202455 (2011).
Paragraph IV Patent Certification Notice for ANDA 202455 (2013).
Paragraph IV Patent Certification Notice for ANDA 202483 (2011).
Paragraph IV Patent Certification Notice for ANDA 202483 (2013).
Paragraph IV Patent Certification Notice for ANDA 202762 (2011).
Paragraph IV Patent Certification Notice for ANDA 203235 (2011).
Paragraph IV Patent Certification Notice for ANDA 203235 (2013).
Paragraph IV Patent Certification Notice for ANDA 203915, Jul. 26, 2013, 63 pgs.
Patent Owner Response for Inter Partes Review, IPR2016-01027 of U.S. Pat. No. 9,060,976, dated Aug. 12, 2016, 81 pages.
Patent Owner Response for Inter Partes Review, IPR2016-01028 of U.S. Pat. No. 9,060,976, dated Aug. 12, 2016, 74 pages.
Patent Owner Response for Inter Partes Review, IPR2016-01412 of U.S. Pat. No. 9,034,376, dated Nov. 18, 2016, 77 pages.
Patent Owner Response for Inter Partes Review, IPR2016-01413 of U.S. Pat. No. 9,034,376, dated Oct. 21, 2016, 74 pages.
Petition for Inter Partes Review, IPR2016-01412 of U.S. Pat. No. 9,034,376, dated Jul. 15, 2016, 75 pages.
Petition for Inter Partes Review, IPR2016-01413 of U.S. Pat. No. 9,034,376, dated Jul. 15, 2016, 66 pages.
Petition for Inter Partes Review, IPR2016-00849 of U.S. Pat. No. 8,389,007, dated Apr. 6, 2016, 73 pages.
Petition for Inter Partes Review, IPR2016-01027 of U.S. Pat. No. 9,060,976, dated May 11, 2016, 70 pages.
Petition for Inter Partes Review, IPR2016-01028 of U.S. Pat. No. 9,060,976, dated May 11, 2016, 70 pages.
Philip, George, et al., "The Human Nasal Response to Capsaicin," J. Allergy Clin. Immonul., vol. 94, No. 6, Part 1, Dec. 1994, pp. 1035-1045, Mosy-Year Book, Inc., Baltimore, MD, United States.
Sarkar, N., "Kinetics of thermal gelation of methylcellulose and hydroxypropylmethylcellulose in aqueous solutions," Carbohydrate Polymers, vol. 26, No. 3, Jan. 1995, pp. 195-203.
Sarkar, N., "Thermal Gelation Properties of Methyl and Hydroxypropyl Methylcellulose," Journal of Polymer Science, vol. 24, No. 4, Aug. 1979, pp. 1073-1087.
Stafford, J.W., et al., "Temperature dependence of the disintegration times of compressed tablets containing hydroxypropylcellulose as binder," Journal of Pharmacy and Pharmacology, vol. 30, No. 1, Sep. 1978, pp. 1-5, John Wiley & Sons, New York, United States.
The 1997 Physician's Desk Reference ("PDR"), 51s, edition, Nov. 1996, pp. 955-957, 988-989, 2163-2167, 2366-2367, Medical Economics Company, Inc., Montvale, NJ, United States.
Tough, Paul, "The Alchemy of Oxycontin: From Pain Relief to Drug Addiction," The New York Times, Jul. 29, 2001, 14 pgs.
U.S. Pharmacopeia & National Formulary 24/19, the Standard of Quality, United States Pharmacopeial Convention, Inc., 1999, pp. 1233-1238, 1372-1375, 1941-1951, 2002-2003, 2442-2443, 2493-2498, National Publishing, Philadelphia, PA, United States.
U.S. Pharmacopeia, p. 2206, 1995.
Wilkins, Jeffrey, N., "Pharmacotherapy of Schizophrenia Patients with Comorbid Substance Abuse," Schizophrenia Bulletin, vol. 23, No. 2, 1997, pp. 215-228.
Woodburn, K.R., et al., "Vascular Complications of Injecting Drug Misuse," British Journal of Surgery, 1996, Vo. 83, oa. 1329-1334.
Yang, et al., "Characterization of Compressibility and Compactibility of Poly(ethylene oxide) Polymers for Modified Release Application by Compaction Simulator," Journal of Pharmaceutical Sciences, vol. 85, No. 10, Oct. 1996, pp. 1085-1090.
Zasypkin, et al., *Multicomponent biopolymer gels*, Food Hydrocolloids, 1997, 11(2): 159-170.
Zhang, F., et al., "Properties of Sustained-Release Tablets Prepared by Hot-Melt Extrusion," Pharmaceutical Development and Technology, vol. 4, No. 2, pp. 241-250 (1999).
Zhang, Feng, Dissertation: "Hot-Melt Extrusion as a Novel Technology to Prepare Sustained-Release Dosage Forms," The University of Texas at Austin, pp. v-xxv, 1-260, Dec. 1999, UMI Microform 9959618, Bell & Howell Information and Learning Company, Ann Arbor, MI, United States.
U.S. Mesh vs. Micron, Filterbag.com, 5 pages, 1998-2019, retrieved from https://www.filterbag.com/U-S-Mesh-vs-Micron-21.html on Sep. 15, 2019.

* cited by examiner

PROCESS OF MAKING STABLE ABUSE-DETERRENT ORAL FORMULATIONS

CROSS-REFERENCE TO RELATED APPLICATION

This application is a continuation of U.S. application Ser. No. 15/950,656, filed on Apr. 11, 2018, which is a continuation of U.S. application Ser. No. 15/649,024, now U.S. Pat. No. 9,968,598, filed on Jul. 13, 2017, which is a continuation of U.S. application Ser. No. 15/255,859, now U.S. Pat. No. 9,737,530, filed on Sep. 2, 2016, which claims the benefit of priority to U.S. Provisional Patent Application No. 62/353,839 filed Jun. 23, 2016, the disclosures of each of which are hereby incorporated by reference in their entirety for all purposes.

FIELD

The present disclosure is generally directed to the field of pharmaceutical compositions, such as compositions designed to reduce the potential for improper administration of drugs that are subject to abuse, extended-release compositions, methods of making such compositions with improved dissolution stability, and methods of using the same for treatment of pain.

BACKGROUND

Opioids such as oxycodone in the form of extended-release (ER) formulations are used to manage moderate to severe chronic pain. Although usually a safe and effective treatment option for patients with chronic pain who are appropriately managed and monitored, ER opioid formulations are associated with high rates of misuse, abuse, and diversion. This is in large part because oral ER opioids carry a large opioid load. Abusers often manipulate (e.g., cut, crush, or dissolve) ER formulations to more rapidly release most, if not all, of the active drug, with the goal of achieving a quick drug high. Further, misuse can occur when patients or their caregivers manipulate ER formulations for any number of reasons, including to reduce the dose or make the medication easier to swallow. Manipulation of most ER opioid formulations, regardless of intent, can result in greater exposure to drug than intended, which can lead to adverse consequences or even death. These challenges have led to the development of ER opioid formulations with properties intended to make product manipulation more difficult. Often referred to as abuse-deterrent, many of these formulations incorporate physical or chemical barriers to mechanical or chemical manipulations.

The DETERx® platform technology is an abuse-deterrent formulation strategy which consists of an active drug dissolved or dispersed in a melt comprising a hydrophobic fatty acid and a wax matrix (optionally including other excipients) that is then formed into particles, for example microspheres, e.g., using a spinning disk or other suitable atomizing or milling process. The microparticles (or microspheres, if produced by a process resulting in spherical particles), along with small quantities of external processing excipients are encapsulated into hard shell capsules or other suitable dosage forms. The microparticles are designed to preserve the extended release characteristics on physical manipulation by means such as crushing with household tools or by chewing. These properties are a consequence of the small size of the extended-release microparticles, along with the physiochemical properties of the inactive ingredients. Additionally, the fatty acid and active ingredient component of DETERx microspheres are selected such that they are associated via an ionic interaction (i.e., salt) in the solid microparticles. This interaction allows the active component to be dissolved during the melt formulation process, and allows for the formation of a solid solution. The creation of a solid solution of drug in hydrophobic materials further reduces the extractability and contributes to the abuse-deterrent properties of the formulation.

The microspheres in oxycodone DETERx are produced using a spray-congealing process from a hot melt. When using a spray congealing process, such as a spinning disk atomization process, the microspheres are formed nearly instantaneously as the melt is atomized. For pharmaceutical products, changes to the product during the normal product shelf-life at recommended storage conditions (i.e., room temperature) should be minimized to the extent possible. For this reason, pharmaceutical products are routinely tested by subjecting the product to stability studies in the commercial packaging configuration. Stability study requirements are outlined in US Food and Drug Administration (FDA) and International Conference on Harmonization (ICH) guidances, including ICH Q1A(R2), "Stability Testing of New Drug Substances and Products", November 2003. Product attributes tested during stability studies include, for example, tests for potency, purity, microbial attributes and drug release rate using standardized dissolution apparatus.

The present invention relates to a process for manufacturing extended-release microparticles with improved dissolution stability. The process of the present invention is related to microparticles comprising an active drug, one or more fatty acids and one or more wax components manufactured by congealing from a hot-melt process. It has been unexpectedly found that curing the product at one or more temperatures within the range from 25° C. up to an inversion temperature, for a minimum period of time, is required to effectively stabilize the dissolution profiles of such compositions. Curing outside this range will have either no significant effect or an adverse effect on product stability. The existence or identification of this inversion temperature and its role in curing has not previously been disclosed for such formulations.

The present inventors have developed a manufacturing process that utilizes curing within a specific temperature range to produce pharmaceutical compositions with improved dissolution stability. This process can be applied in making pharmaceutical formulations containing active drugs, such as opioids.

SUMMARY OF THE DISCLOSURE

This disclosure provides a process of making abuse-deterrent pharmaceutical formulations. In one embodiment, the process requires forming an abuse-deterrent formulation and then curing the composition. In one embodiment, the process of making an abuse-deterrent formulation comprises the steps of: preparing a mixture comprising (i) one or more pharmaceutically acceptable waxes, one or more drugs, and one or more pharmaceutically acceptable fatty acids, or (ii) one or more drugs in the form of a fatty acid salt, one or more pharmaceutically acceptable waxes, at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours.

In one embodiment of the disclosed process, the cured microparticles or cured formulated microparticles exhibit less change in the dissolution profile after storing for 6 months at 25° C. and 60% relative humidity (RH) than otherwise identical uncured formulated microparticles after storing for 6 months at 25° C. and 60% RH when dissolution is conducted at 100 RPM using USP Apparatus I in 900 mL of pH 4.5 sodium acetate buffer supplemented with 0.03% Tween 20 at 37° C.

In one embodiment of the disclosed process, the cured microparticles or cured formulated microparticles exhibit less than a 15% change in the mean percent drug released at the 4 hour dissolution time point after storage for 6 months at 25° C. and 60% RH. In another embodiment, the cured microparticles or cured formulated microparticles exhibit less than a 10% change in the mean percent drug released at the 4 hour dissolution time point after storage for 6 months at 25° C. and 60% RH. In another embodiment, the cured microparticles or cured formulated microparticles exhibit less than a 5% change in the mean percent drug released at the 4 hour dissolution time point after storage for 6 months at 25° C. and 60% RH. In other embodiments, the cured microparticles or cured formulated microparticles exhibit less than a 2.5% change in the mean percent drug released at the 4 hour dissolution time point after storage for 6 months at 25° C. and 60% RH.

In one embodiment of the disclosed process, the fatty acid is myristic acid, the drug is oxycodone, and the inversion temperature is approximately 36° C.

In another embodiment of the disclosed process, the fatty acid is stearic acid, the drug is oxycodone, and the inversion temperature is approximately 53° C.

In one embodiment of the disclosed process, the microparticles are cured at a first temperature above the inversion temperature and subsequently a second temperature below the inversion temperature.

In one embodiment, the present disclosure provides a pharmaceutical composition prepared by the process comprising the steps of: a) mixing one or more drugs, one or more pharmaceutically acceptable waxes, and one or more pharmaceutically acceptable fatty acids at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours. In another embodiment, the present disclosure provides a pharmaceutical composition prepared by the process comprising the steps of: a) mixing one or more fatty acid salts of one or more drugs, one or more pharmaceutically acceptable waxes, at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours. In another embodiment, a pharmaceutical composition comprises a composition prepared by any of the processes described herein, for example wherein the fatty acid is myristic acid, the drug is oxycodone, and the inversion temperature is approximately 36° C.

In another embodiment of the present disclosure, a capsule is provided comprising any one of the pharmaceutical compositions as described herein.

This disclosure provides a pharmaceutical formulation with improved dissolution stability. In one embodiment, the pharmaceutical formulation is a cured composition. In some embodiments, the cured composition is in a form of solid microparticles or formulated microparticles. In one embodiment, the pharmaceutically acceptable solid microparticles or formulated microparticles cured at one or more temperatures within the range of 25° C. up to and including the inversion temperature, for a minimum of about 48 hours comprise: a mixture of one or more drugs, one or more waxes, and a sufficient amount of one or more fatty acids to provide said mixture in substantially homogenous form during the melt manufacture of the microparticles.

In one embodiment of the disclosed microparticles, the fatty acid is myristic acid, and the drug is oxycodone.

This disclosure provides a method of treating pain comprising administering any one of the pharmaceutical compositions as described herein. In some embodiments of the methods disclosed herein, the pharmaceutical composition is prepared by the process comprising the steps of: a) preparing a mixture comprising (i) one or more drugs, one or more pharmaceutically acceptable waxes, and one or more pharmaceutically acceptable fatty acids, or (ii) one or more drugs in the form of a fatty acid salt and one or more pharmaceutically acceptable waxes at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours; wherein the fatty acid is myristic acid, the drug is oxycodone, and the inversion temperature is approximately 36° C.

In another embodiment of the method disclosed herein, a capsule comprising any one of the pharmaceutical compositions as disclosed herein is provided.

In another embodiment of the present disclosure, the method of treating pain is provided, wherein pharmaceutically acceptable solid microparticles or formulated microparticles cured at one or more temperatures within the range of 25° C. up to and including the inversion temperature, for a minimum of about 48 hours, as described herein, e.g. comprising: a mixture of one or more drugs, one or more waxes, and a sufficient amount of one or more fatty acids to provide said mixture in substantially homogenous form during the melt manufacture of the microparticles, is administered to a patient in need thereof. In one embodiment, the method of treating pain as disclosed herein comprises administering a pharmaceutically acceptable microparticles or formulated microparticles comprising myristic acid and oxycodone.

DETAILED DESCRIPTION OF THE FIGURES

FIG. 1. shows dissolution of capsules produced with uncured oxycodone containing microspheres after storage at 25° C./60% RH, 30° C./65% RH, and 40° C./75% RH for 3 months.

Figure 2A:
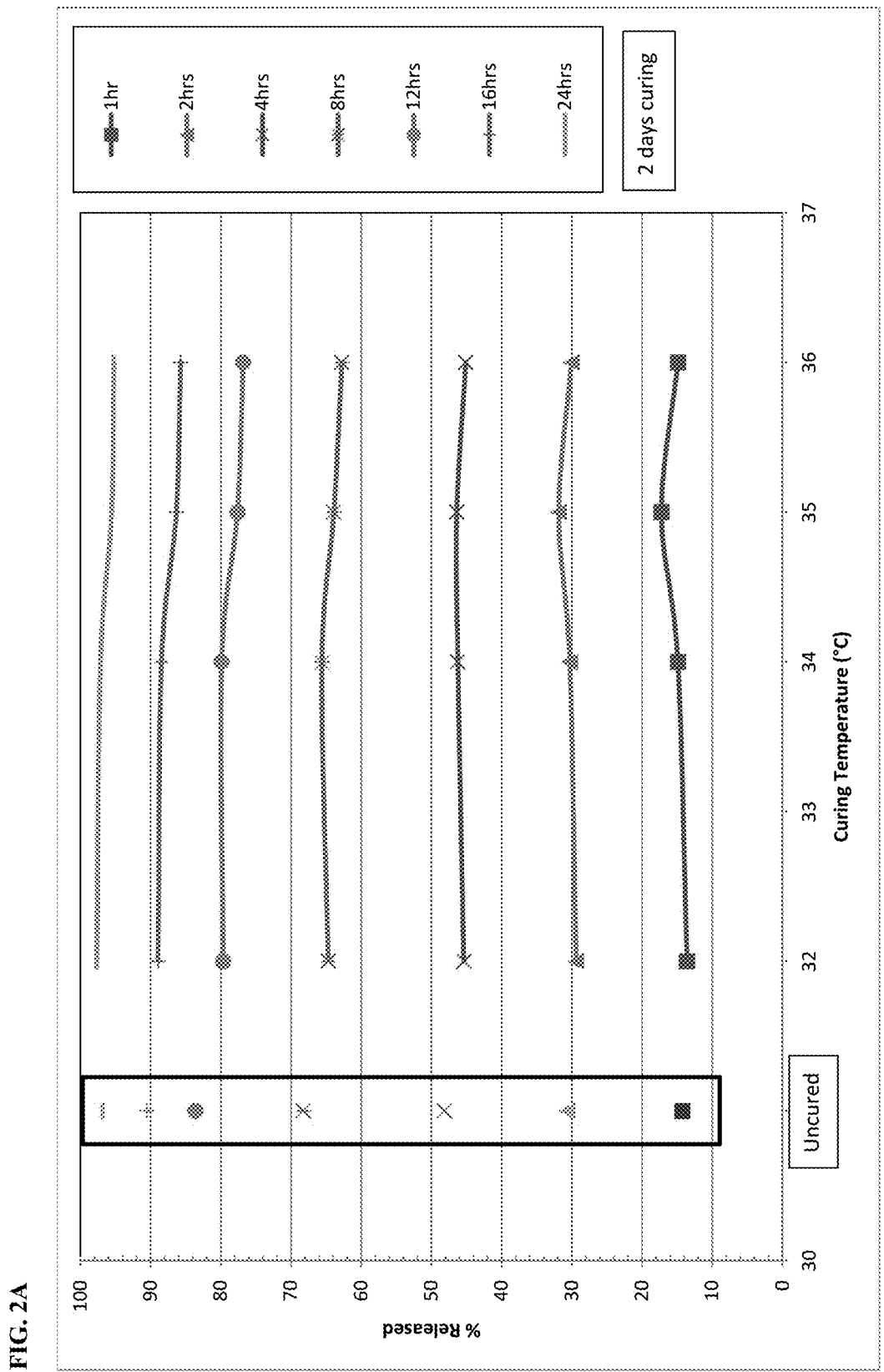

FIG. 2A. shows dissolution of capsules produced with oxycodone containing microspheres after single-stage curing between 32-36° C. for 2 days.

Figure 2B:
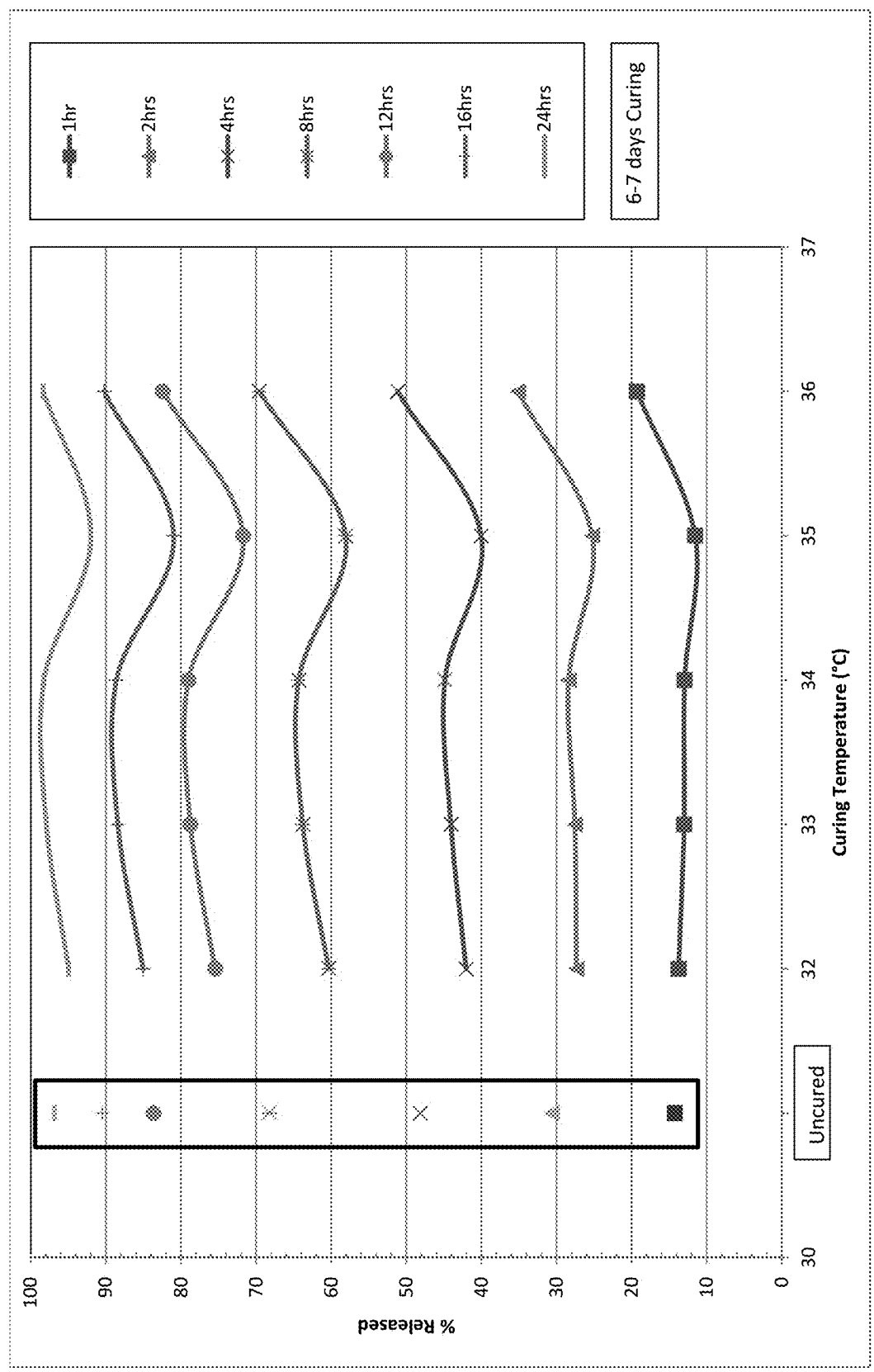

FIG. 2B. shows dissolution of capsules produced with oxycodone containing microspheres after single-stage curing between 32-36° C. for 6-7 days.

Figure 3A:
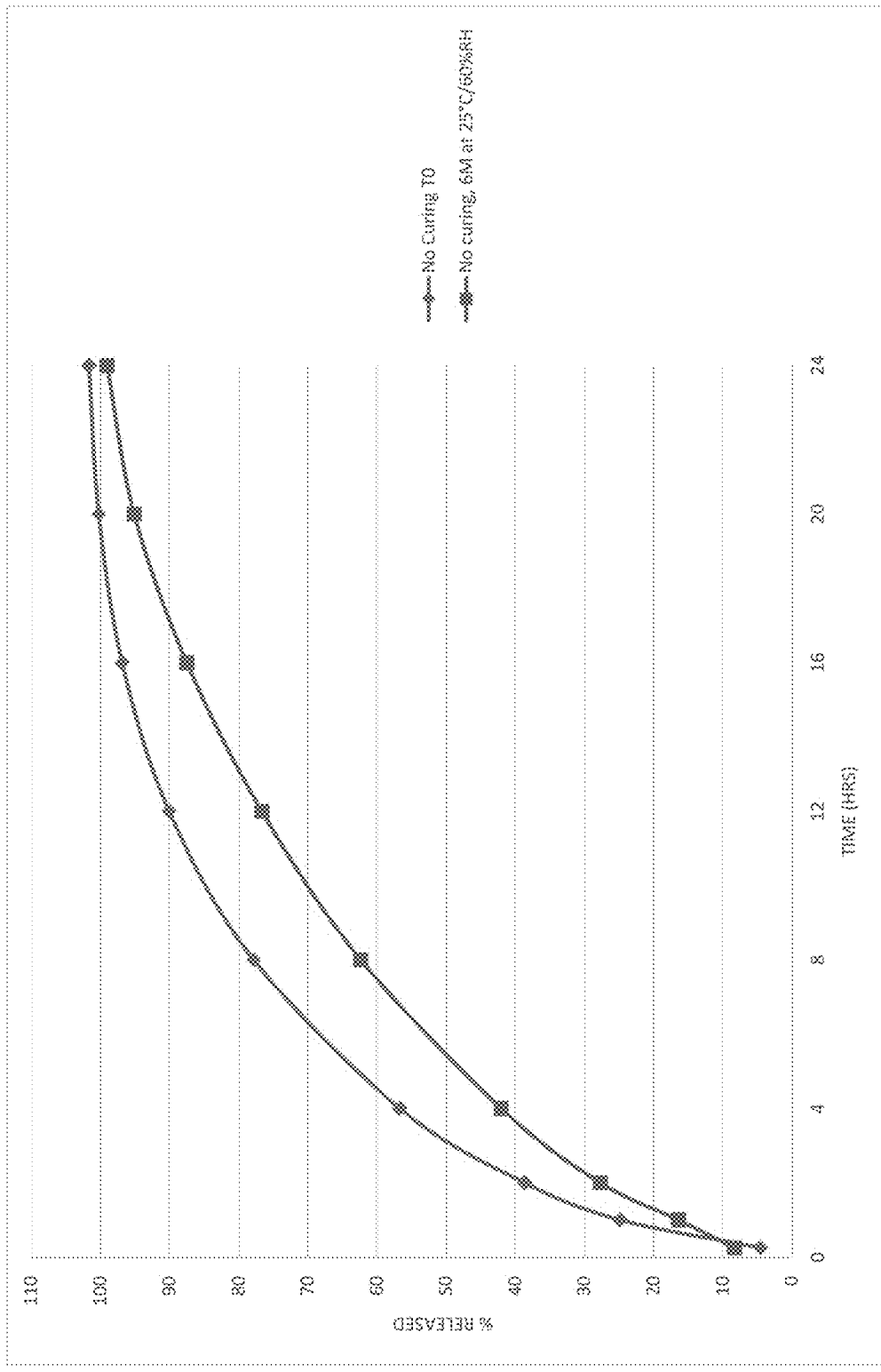

FIG. 3A. compares initial (T0) dissolution of a formulation of uncured oxycodone containing microspheres with dissolution of the same uncured formulation after 6 months of storage at 25° C./60% RH.

Figure 3B:
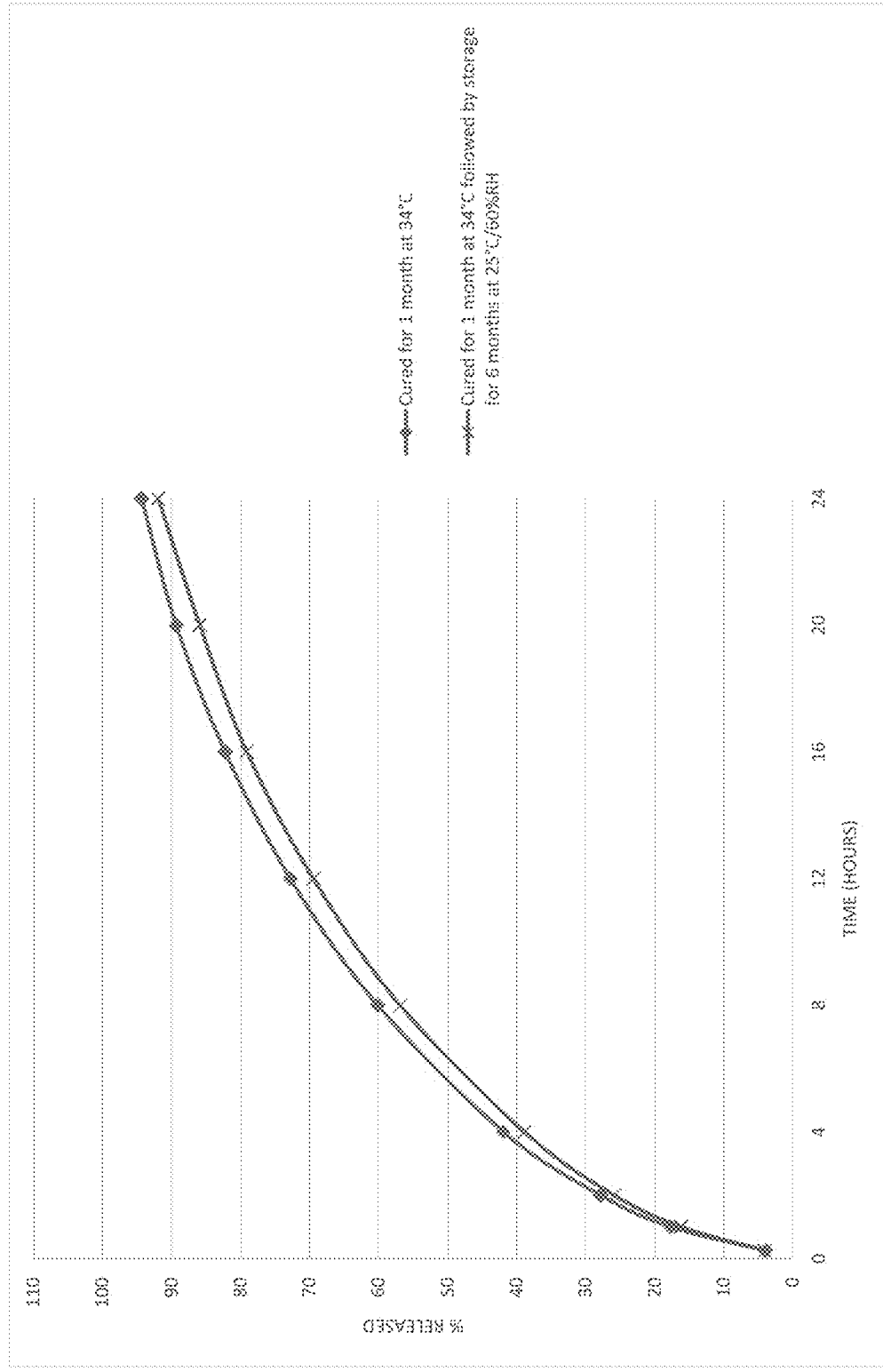

FIG. 3B. compares initial (T0) dissolution of a formulation of oxycodone containing microspheres cured in a single stage at 34° C. for 1 month with dissolution of the same cured formulation after 6 months of storage at 25° C./60% RH.

Figure 3C:
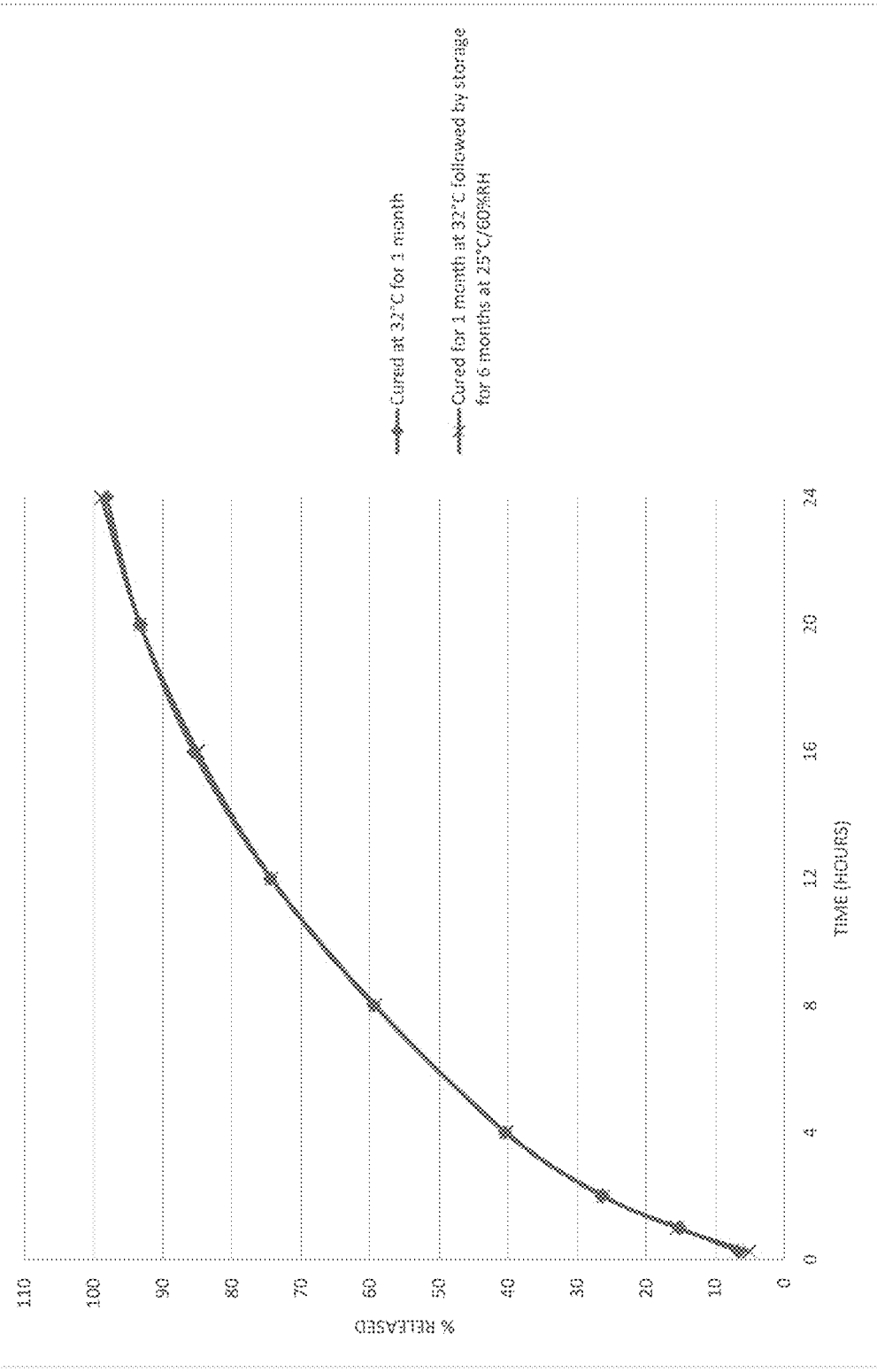

FIG. 3C. compares initial (T0) dissolution of a formulation of oxycodone containing microspheres cured in a single stage at 32° C. for 1 month with dissolution of the same cured formulation after 6 months of storage at 25° C./60% RH.

Figure 3D:
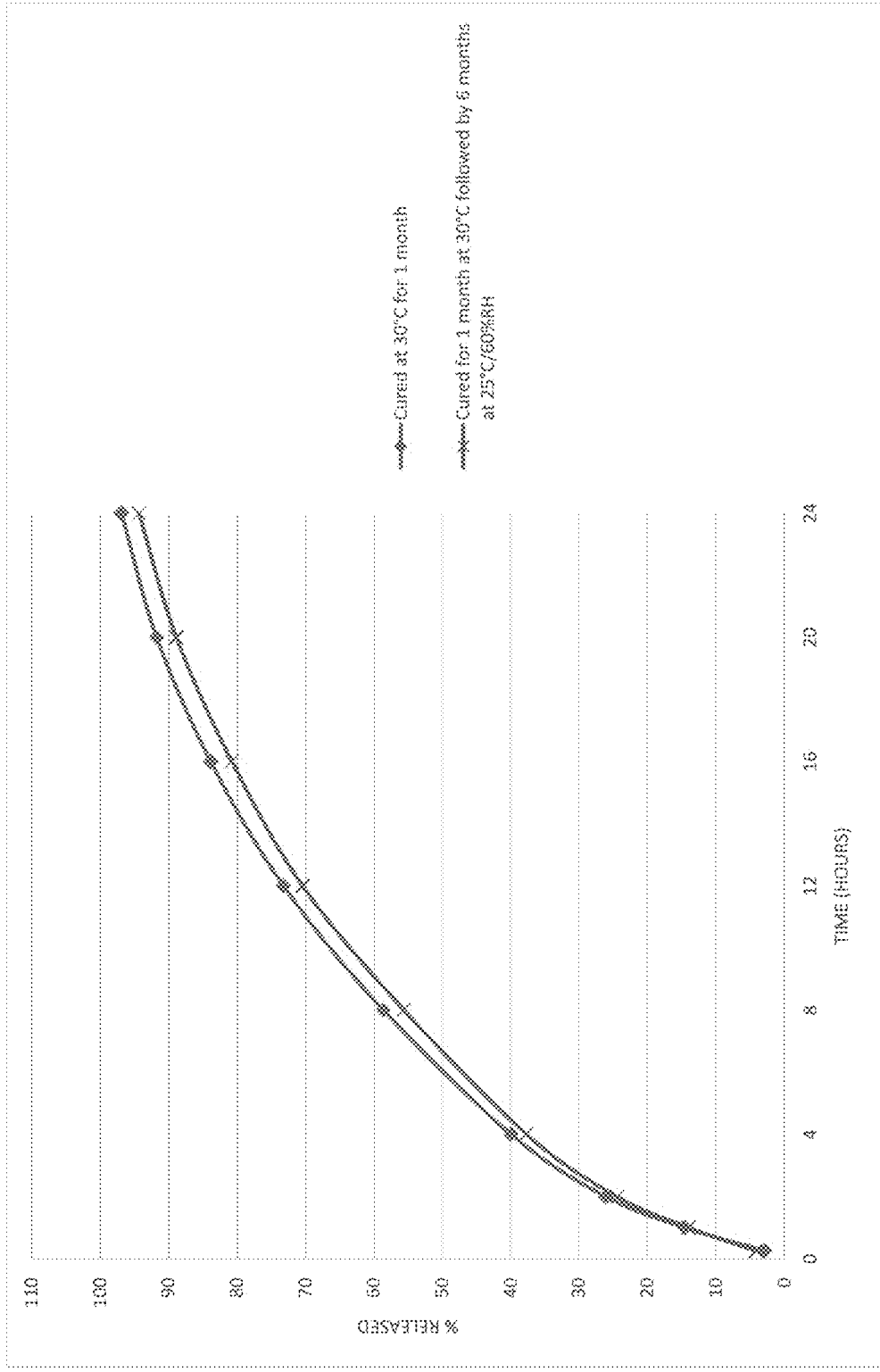

FIG. 3D. compares initial (T0) dissolution of a formulation of oxycodone containing microspheres cured in a single stage at 30° C. for 1 month with dissolution of the same cured formulation after 6 months of storage at 25° C./60% RH.

Figure 3E:
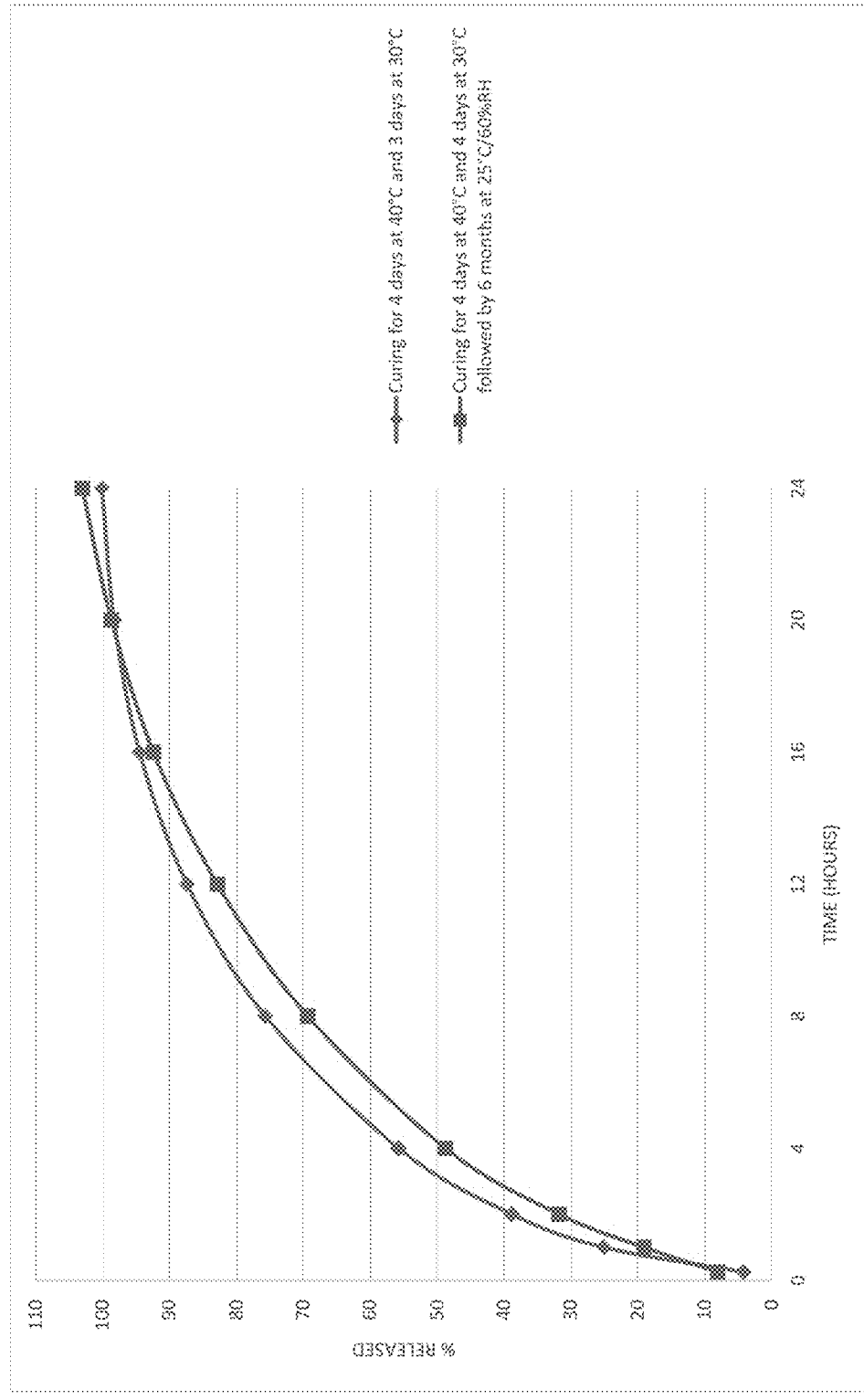

FIG. 3E. compares initial (T0) dissolution of a formulation of oxycodone containing microspheres cured in a 2-stage process (40° C./4 d:30° C./3 d) with dissolution of the same cured formulation after 6 months of storage at 25° C./60% RH.

Figure 4A:
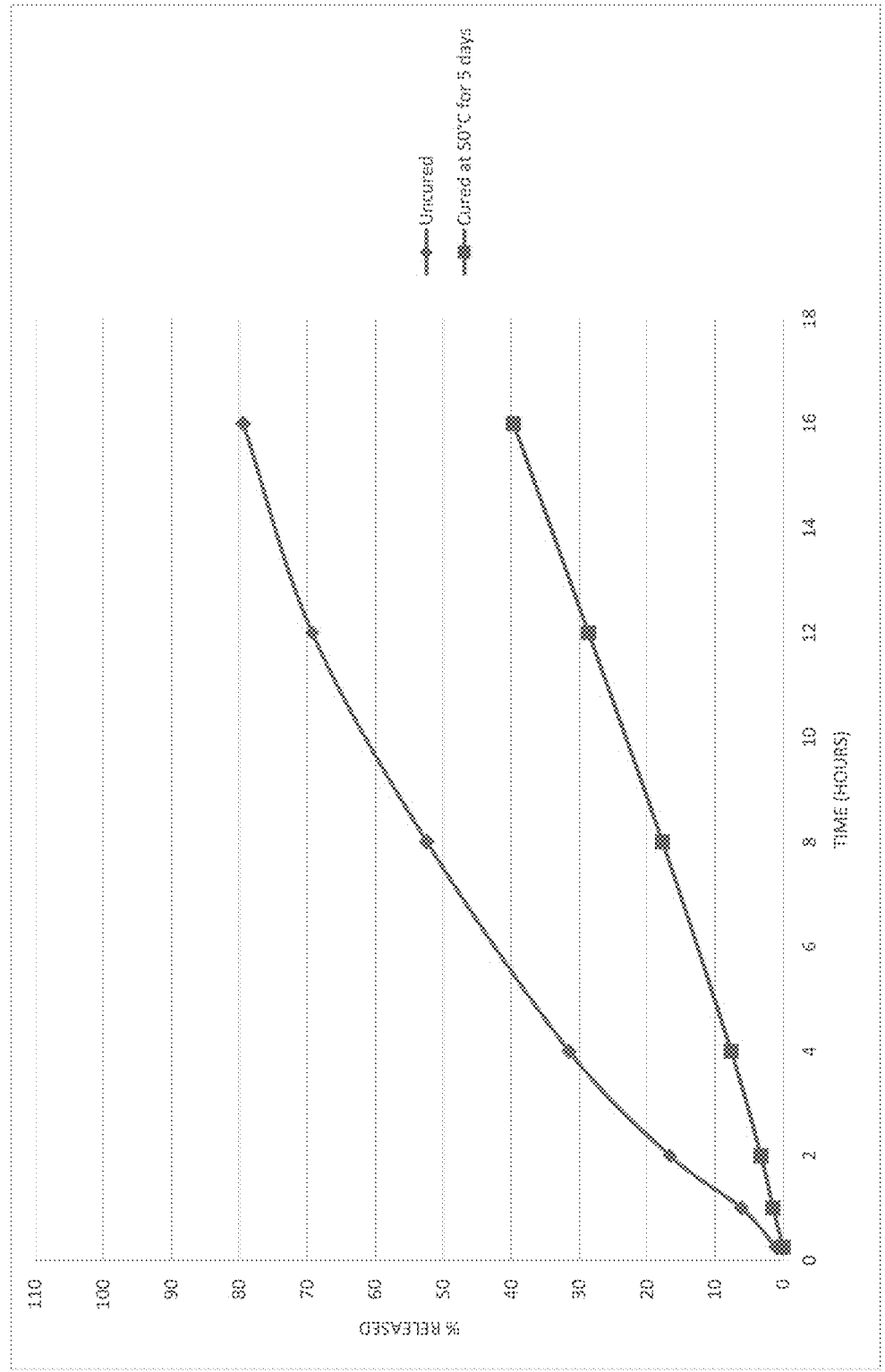

FIG. 4A. shows the dissolution behavior of a formulation of microspheres containing oxycodone and stearic acid after single stage curing at 50° C.

Figure 4B:
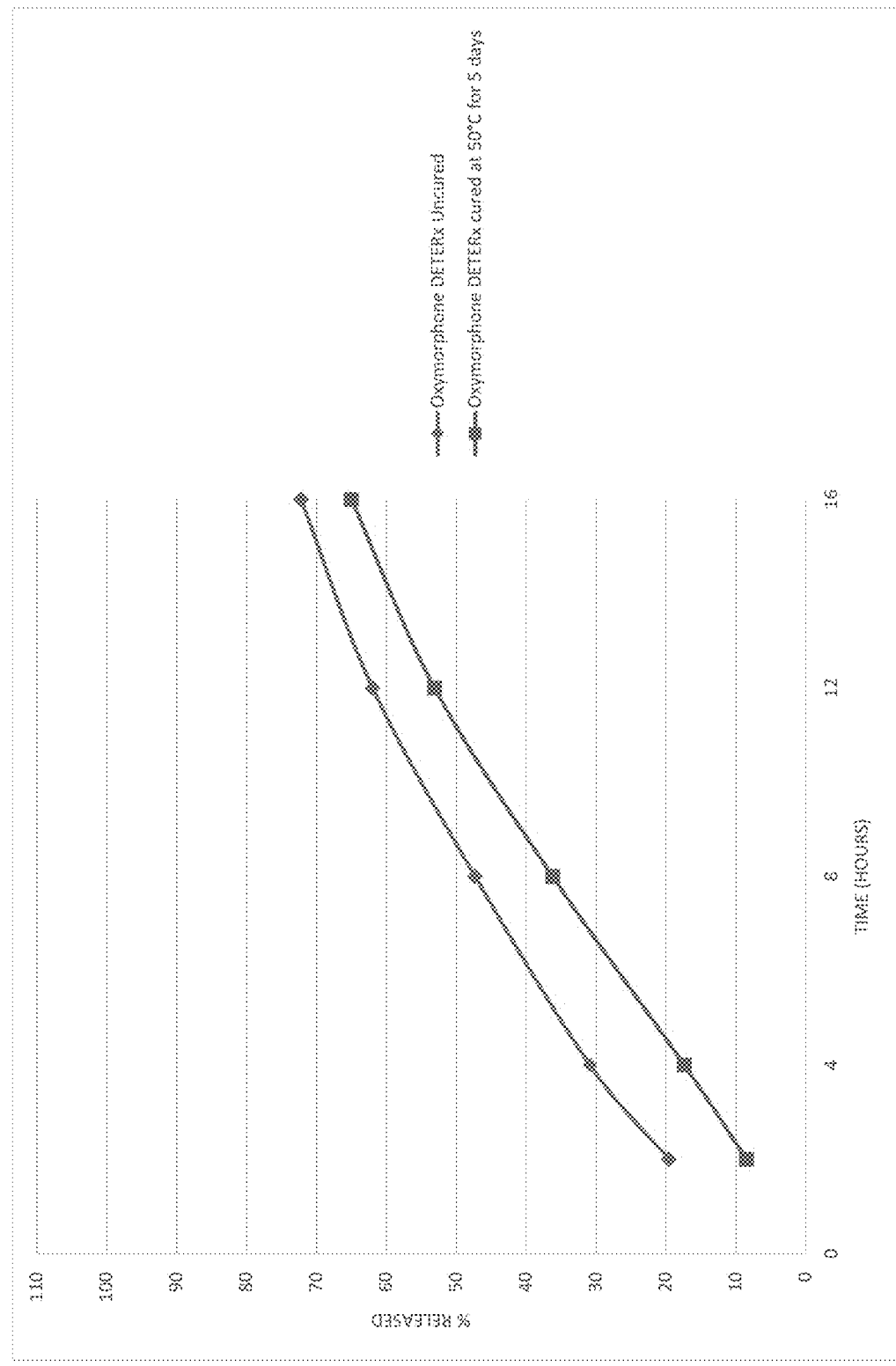

FIG. 4B. shows the dissolution behavior of a formulation of microspheres containing oxymorphone and stearic acid after single stage curing at 50° C.

Figure 4C:
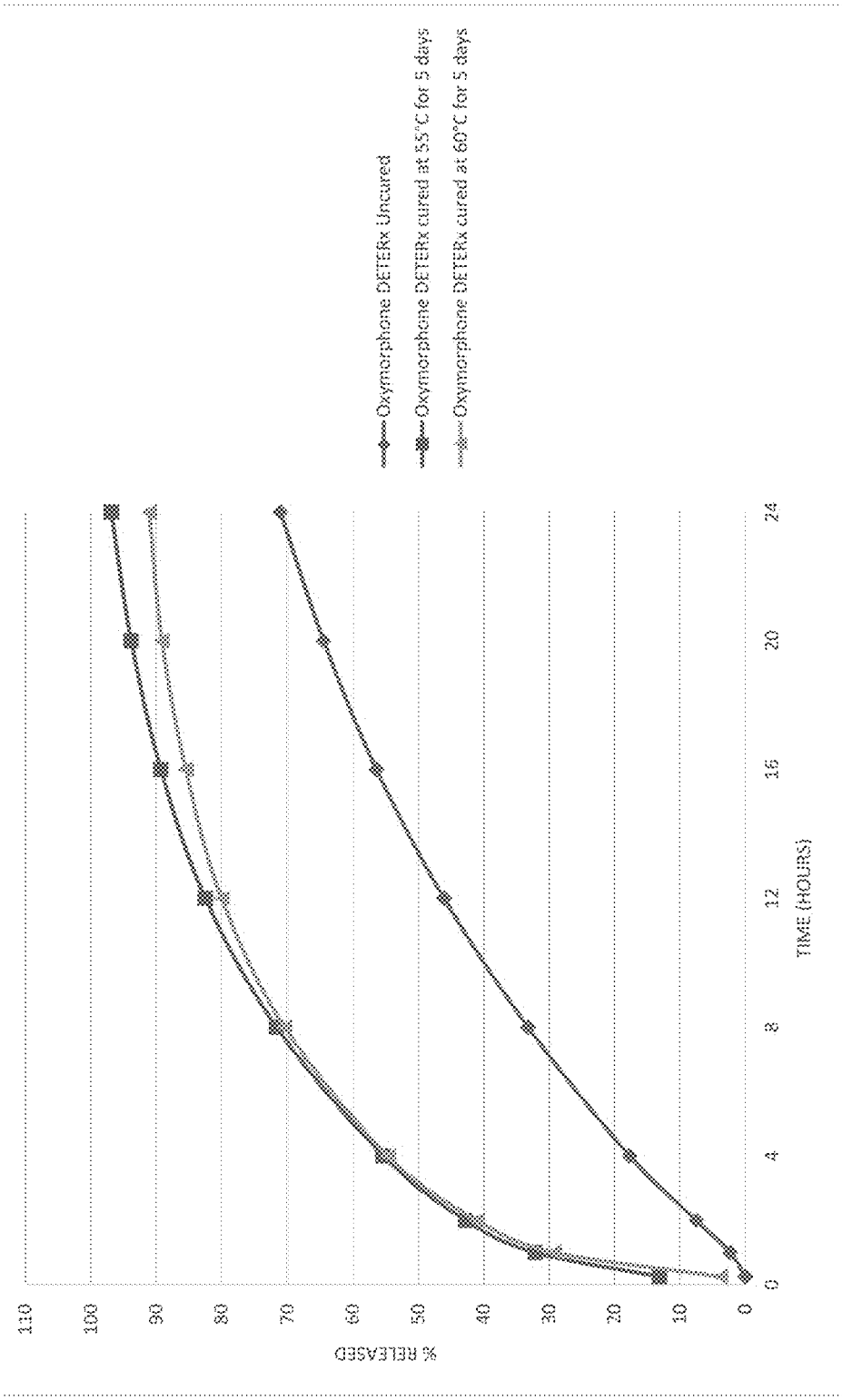

FIG. 4C. shows the dissolution behavior of formulation of microspheres containing oxymorphone and stearic acid after single stage curing at 55° C. and 60° C.

DETAILED DESCRIPTION OF THE DISCLOSURE

Definitions

While the following terms are believed to be well understood by one of ordinary skill in the art, the following definitions are set forth to facilitate explanation of the presently disclosed subject matter.

The term "a" or "an" refers to one or more of that entity; for example, "a halogen" refers to one or more halogens or at least one halogen. As such, the terms "a" (or "an"), "one or more" and "at least one" are used interchangeably herein. In addition, reference to "an alkyl group" by the indefinite article "a" or "an" does not exclude the possibility that more than one of the alkyl group is present, unless the context clearly requires that there is one and only one of the alkyl groups.

As used herein, the verb "comprise" as is used in this description and in the claims and its conjugations are used in its non-limiting sense to mean that items following the word are included, but items not specifically mentioned are not excluded.

As used herein, "curing" or "annealing" refers to a process used to stabilize excipients, intermediates and finished products over shorter time frames than would otherwise be realized at room temperature, for example by heating or maintaining under specified temperature, time, and, optionally, RH conditions.

As used herein, "formulated" (in the context of "formulated" microparticles) refers to microparticles (cured or uncured) combined with other excipients and/or further processed by means such as, but not limited to, tableting by compression or encapsulation.

As used herein "inversion temperature" is the temperature at or below which a composition of the present invention is cured to result in improved dissolution stability as described herein. The inversion temperature of a particular composition of the present invention can be determined empirically, e.g., as described in Example 2 herein.

The fatty acid salt is formed by interaction between the one or more fatty acids and one or more drugs wherein the fatty acid is present in excess of or below the concentration required for complete solubilization of the drugs in the melt. The fatty acid salt is dispersed within a wax composition and, optionally, other excipients in a solid, dissolved or melted state. As used herein, "substantially homogenous" with respect to the molten compositions or microparticles of the present disclosure refers specifically to the homogeneity of the fatty acid salt(s) of the one or more drugs in the waxy excipients. A substantially homogeneous combination of the fatty acid salt(s) of the one or more drugs and one or pharmaceutically acceptable waxes and other excipients means at least 50 mole % of the drug is homogeneously dissolved or dispersed in the wax composition. In other embodiments, the mole % of fatty acid salt of the drug dissolved or dispersed in the wax is at least 55%, 60%, 65%, 70%, 75%, 80%, 85%, 90%, 95%, 97%, 99%, or about 100%

As used herein, a "wax" or a "wax-like material" is defined as any pharmaceutically acceptable material, including any of a diverse class of organic compounds that are hydrophobic, malleable solids near ambient temperatures. They include higher alkanes and lipids, typically with melting points above about 40° C. (104° F.), melting to give low viscosity liquids. Waxes are virtually insoluble in water. Natural waxes of different types are produced by plants and animals and occur in petroleum and include those waxes disclosed herein.

As used herein, the symbol "≤" means "not more than" or "equal to or less than"; "<" means "less than"; "≥" means "not less than" or "equal to or more than"; and ">" means "more than". Furthermore, the numerical numbers, when used herein in connection with purity or impurity content, include not only the exact number but also the approximate range around the number. For example, the phrase "purity of 99.0%" denotes a purity of about 99.0%.

Pharmaceutical Compositions

The present disclosure provides a pharmaceutical composition designed to reduce the potential for improper administration of drugs that are subject to abuse. In one embodiment, the composition is in the form of or comprises microparticles formed from a melt manufacturing process. In another embodiment, the composition or a component of the composition is cured. In another embodiment, the composition of the present disclosure provides improved dissolution stability.

In one embodiment, a pharmaceutical composition of the present disclosure is or comprises solid microparticles. In one embodiment, pharmaceutically acceptable solid microparticles or formulated microparticles cured at a temperature within the range of 25° C. up to and including the inversion temperature, for a minimum of about 48 hours comprise: a mixture of one or more drugs, one or more waxes, and a sufficient amount of one or more fatty acids to provide said mixture in substantially homogenous form during the melt manufacture of the microparticles.

In one embodiment, one or more drugs are selected from Schedule II, III, IV or V drugs. In another embodiment, the one or more drugs are opioid analgesics.

In one embodiment, one or more drugs are selected from 1-phenylcyclohexylamine, 1-piperidinocyclohexanecarbonitrile, alfentanil, alphacetylmethadol, alphaprodine, alprazolam, amobarbital, amphetamine, anileridine, apomorphine, aprobarbital, barbital, barbituric acid derivatives, bemidone, benzoylecgonine, benzphetamine, betacetylmethadol, betaprodine, bezitramide, bromazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecgonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethadol, levomethadone, levomethadyl acetate, levomethorphan, levorphanol, lofentanil, loperamide, loprazolam, lorazepam, lormetazepam, lysergic acid, lysergic acid amide, mazindol, medazepam, mefenorex, mepetidine, meptazinol, metazocine, methadone, methamphetamine, methohexital, methotrimeprazine, methyl dihydromorphinone, methylphenidate, methylphenobarbital, metopon, morphine, nabilone, nalbuphine, nalbupine, nalorphine, narceine, nefopam, nicomorphine, nimetazepam, nitrazepam, nordiazepam, normethadone, normorphine, oxazepam, oxazolam, oxycodone, oxymorphone, pentazocine, pentobarbital, phenadoxone, phenazocine, phencyclidine, phendimetrazine, phenmetrazine, phenetidine, piminodine, prodilidine, properidine, propoxyphene, racemethorphan, racemorphan, racemoramide, remifentanil, secobarbital, sufentanil, talbutal, thebaine, thiamylal, thiopental, tramadol, trimeperidine, or vinbarbital, or a pharmaceutically acceptable salt or a stereoisomer thereof.

In addition, in one embodiment, the following scheduled drugs may be incorporated into the composition: allobarbitone, alprazolam, amylobarbitone, aprobarbital, barbital, barbitone, benzphetamine, brallobarbital, bromazepam, brotizolam, buspirone, butalbital, butobarbitone, bntorphanol, camazepam, captodiame, carbromal, carfentanil, carpipramine, cathine, chloral, chloral betaine, chloral hydrate, chloralose, chlordiazepoxide, chlorhexadol, chlormethiazole edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, enciprazine, estazolam, ethyl loflazepate, etizolam, febarbamate, fencamfamin, fenfluramine, fenproporex, fluanisone, fludiazepam, flunitraam, flunitrazepam, flurazepam, flutoprazepam, gepirone, glutethimide, halazepam, haloxazolam, hexobarbitone, ibomal, ipsapirone, ketazolam, loprazolam mesylate, lorazepam, lormetazepam, mazindol, mebutamate, medazepam, mefenorex, mephobarbital, meprobamate, metaclazepam, methaqualone, methohexital, methylpentynol, methylphenobarbital, midazolam, milazolam, morphine, nimetazepam, nitrazepam, nordiazepam, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibarbal, quazepam, quinalbaritone, secobarbital, secbutobarbitone, sibutramine, temazepam, tetrazepam, triazolam, triclofos, zalepan, zaleplon, zolazepam, zolpidem, or zopiclone, or a pharmaceutically acceptable salt or a stereoisomer thereof.

The composition disclosed herein contemplates all such compounds, including cis- and trans-isomers, R- and S-enantiomers, diastereomers, (D)-isomers, (L)-isomers, the racemic mixtures thereof, compounds of different spacial conformations, and other mixtures thereof, as falling within the scope of the invention. Additional asymmetric carbon atoms may be present in a substituent such as an alkyl group. All such isomers, as well as mixtures thereof, are intended to be included in this disclosure.

In one embodiment, the one or more drugs is oxycodone or pharmaceutically acceptable salt thereof. In another embodiment, the one or more drugs is oxycodone hydrochloride. In a further embodiment the one or more drugs is a fatty acid salt of oxycodone. Suitable fatty acids include any of the fatty acids disclosed herein.

In one embodiment, the one or more drugs are provided in about 1 wt. % to about 60 wt. % of the pharmaceutical composition or the pharmaceutical microparticles. In another embodiment, the one or more drugs are provided in about 1 wt. % to about 20 wt. % or in about 1 wt. % to about 10 wt. % of the pharmaceutical composition or the pharmaceutical microparticles. In one embodiment, the one or more drugs are provided in about 1, about 2, about 3, about 4, about 5, about 6, about 7, about 8, about 9, about 10, about 11, about 12, about 13, about 14, about 15, about 16, about 17, about 18, about 19, or about 20 wt. % of the pharmaceutical composition or the pharmaceutical microparticles.

In one embodiment, the one or more drugs in a dosage form comprising any one of the compositions disclosed herein contains about 1 to about 100 mg of the drug. In one embodiment, the drug in a dosage form is about 5, 7.5, 10, 15, 20, 25, 30, 35, 40, 45, 50, 55, 60, 65, 70, 75, or 80 mg. In one embodiment, the dosage form comprises oxycodone or pharmaceutically acceptable salts thereof in amounts equivalent to about 9, 13.5, 18, 27, 36, 54, or 72 mg oxycodone base. When the drug is in the form of a salt, the weight percentage of drug salt in the compositions of the present invention is expressed as the equivalent weight of the non-salt (or free-base) form of the drug unless otherwise specified.

In one embodiment, the one or more waxes are selected from wax-like materials including natural or synthetic waxes, hydrocarbons, or normal waxes. Examples of waxes include, but are not limited to, beeswax, glycowax, castor wax, carnauba wax, paraffins and candelilla wax. In one embodiment, the one or more waxes are selected from carnauba wax, beeswax, and combinations thereof.

In one embodiment, the one or more waxes are provided in about 1 wt. % to about 80 wt. % of the pharmaceutical composition or the pharmaceutical microspheres. In another embodiment, the one or more waxes are provided in about 20 wt. % to about 80 wt. % or 30 wt. % to about 50 wt. % of the pharmaceutical composition or the pharmaceutical microparticles. In one embodiment, the one or more waxes are provided in about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60, about 61, about 62, about 63, about 64, about 65, about 66, about 67, about 68, about 69, about 70, wt. % of the pharmaceutical composition or the pharmaceutical microparticles.

In one embodiment, the one or more fatty acids are selected from free fatty acids. In one embodiment, the one or more fatty acids are selected from lauric acid, myristic acid, stearic acid, or palmitic acid, or combinations thereof. In some embodiments, the one or more fatty acids are selected from substituted or unsubstituted C12-C40 fatty acids. In other embodiments, the one or more fatty acids are selected from substituted or unsubstituted C12-C20 fatty acids. In one embodiment, the one or more fatty acid is myristic acid. In other embodiments, the one or more fatty acid is stearic acid. In other embodiments, the one or more fatty acids is palmitic acid. In other embodiments the one or more fatty acids are a combination of palmitic and stearic acids.

In one embodiment, the one or more fatty acids are provided in an amount of about 1 wt. % to about 80 wt. % of the pharmaceutical composition or the pharmaceutical microspheres. In another embodiment, the one or more fatty acids are provided in an amount of about 20 wt. % to about 80 wt. % or 40 wt. % to about 60 wt. % of the pharmaceutical composition or the pharmaceutical microparticles. In one embodiment, the one or more fatty acids are provided in an amount of about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60, about 61, about 62, about 63, about 64, about 65, about 66, about 67, about 68, about 69, or about 70, wt. % of the pharmaceutical composition or the pharmaceutical microparticles.

In one embodiment, the amount of one or more fatty acids sufficient to provide said mixture in substantially homogenous form during melt manufacture is determined by experimentation. In another embodiment, the amount of one or more fatty acids sufficient to provide said mixture in substantially homogenous form is about 40 wt. % to about 60 wt. % of the pharmaceutical composition or the pharmaceutical microparticles. In another embodiment, the amount of one or more fatty acids sufficient to provide said mixture in substantially homogenous form is about 52 wt. % of the pharmaceutical composition or the pharmaceutical microspheres.

In one embodiment, the pharmaceutical composition of the present disclosure further comprises pharmaceutically acceptable excipients.

In one embodiment, suitable pharmaceutically acceptable excipients include fats and fatty substances. Examples of fats and fatty substances include fatty alcohols (such as lauryl, myristyl stearyl, cetyl or cetostearyl alcohol), fatty acid derivatives, including but not limited, fatty acid esters, fatty acid glycerides (mono-, di- and tri-glycerides), fatty amines, and hydrogenated fats. Specific examples include, but are not limited to hydrogenated vegetable oil, hydrogenated cottonseed oil, hydrogenated castor oil, hydrogenated oils available under the trade name Sterotex®, cocoa butter, glyceryl behenate (available under the trade name COMPRITOL 888®), glyceryl dipalmitostearate (available under the trade name PRECIROL®), and stearyl alcohol.

In some embodiments, drug containing multiparticulates are coated. Drug containing multiparticulates can be coated with water insoluble materials, slowly water soluble materials, organic insoluble materials and/or materials with pH dependent solubilities. In general, any coating procedure which provides a contiguous coating on each multiparticulate can be used. Coating procedures known in the arts include, but are not limited to, fluid bed coating processes and microencapsulation. Detailed descriptions of these processes can be found in "Remington—The science and practice of pharmacy", 20th Edition, Jennaro et al., (Phila, Lippencott, Williams, and Wilkens, 2000.

The water-insoluble coating materials may be selected from natural or synthetic film-formers used alone, in admixture with each other, or in admixture with plasticizers, pigments and other substances to alter the characteristics of the coating. A water-insoluble but water-permeable diffusion barrier may contain ethyl cellulose, methyl cellulose and mixtures thereof. The water-permeable diffusion barrier may also include ammonio methacrylate copolymers sold under the trade name EUDRAGIT®. (Rohm Pharma), such as EUDRAGIT RS, EUDRAGIT RL, EUDRAGIT NE and mixtures thereof. Other synthetic polymers, for example, polyvinyl acetate (available under the trade name KOLLICOAT®), can also be used to form water-insoluble but permeable coatings.

Coating materials may also include one or more pH sensitive polymers which are insoluble in the acid environment of the stomach, and soluble in the more basic environment of the GI tract. These coatings, referred to as enteric coatings, create a dosage form designed to prevent drug release in the stomach.

Enteric coated particles can be prepared as described in "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995). Examples of suitable coating materials include, but are not limited to, cellulose polymers, such as cellulose acetate phthalate, hydroxypropyl cellulose, hydroxypropyl methylcellulose phthalate and hydroxypropyl methylcellulose acetate succinate; polyvinyl acetate phthalate, acrylic acid polymers and copolymers, and certain methacrylic resins that are commercially available under the trade name EUDRAGIT®. (Rohm Pharma). Additionally the coating material may contain conventional carriers such as plasticizers, pigments, colorants, glidants, stabilization agents, and surfactants.

In some embodiments, drug containing multiparticulates are blended with extragranular material and filled into hard shell capsules. The extragranular material can serve several functions. One or more extragranular materials, such as lubricants or glidants, can be used to reduce the tendency of the multiparticulates from agglomerating or to provide better flow properties to the formulation. Examples of suitable materials for this purpose include, but are not limited to, magnesium stearate, zinc stearate, colloidal silicone dioxide, talc, starch, calcium stearate, hydrogenated vegetable oils, stearic acid, sodium stearyl fumarate, sodium benzoate, sodium acetate, leucine, sodium oleate, sodium lauryl sulfate, magnesium lauryl sulfate and polyethylene glycol. In one embodiment, the pharmaceutically acceptable excipients include, but are not limited to, silicon dioxide colloidal and magnesium stearate. In other embodiments, the extragranular material is a natural or synthetic gel forming excipient, added to form a gel or viscous environment around the particles when exposed to an aqueous environment. Extragranular material of this type can be used to modulate the release of drug from the dosage form when the dosage form is manipulated (for example for preparation for IV abuse), or in some embodiments when the dosage form is administered intact.

In some embodiments, the compositions are coated with an enteric coating. Enteric coatings known in the art are applied directly to the abuse-deterrent multiparticulate or coated multiparticulate compositions or are applied to the surface of a capsule or tablet containing the abuse deterrent multiparticulate and/or coated multiparticulate compositions. Enteric coatings known in the art include, for example, acrylic polymers that are commercially available under the trade name EUDRAGIT®, cellulose acetate phthalate, hydroxypropylmethyl-cellulose phthalate, polyvinylacetate phthalate, shellac, hydroxypropyl-methylcellulose succinate, cellulose acetate trimellitate or mixtures thereof. In one embodiment, the particles are coated with cellulose acetate phthalate.

Dosage forms can include one or more drugs. When the dosage form includes two or more drugs they can be Scheduled drugs or can be a combination of Scheduled and non-Scheduled drugs. The drugs can be incorporated into the same multiparticulates. Alternatively, the drugs can be incorporated into separate multiparticulate compositions where the Scheduled drugs are incorporated into abuse deterrent multiparticulate compositions and the non-Scheduled drugs are incorporated into abuse deterrent multiparticulate compositions, sustained release compositions known in the art or immediate release compositions known in the art. The compositions containing the different drugs can be formulated into a single solid dosage form suitable for oral administration; for example, they can be incorporated into a hard capsule shell, or combined with appropriate excipients and compressed into a tablet form.

Examples of non-scheduled drugs that may be included in dosage forms described herein include, but are not limited to, aspirin, acetaminophen, non-steroidal anti-inflammatory drugs, cyclooxygenase II inhibitors, N-methyl-D-aspartate receptor antagonists, glycine receptor antagonists, triptans, dextromethorphan, promethazine, fiorinal, guaifenesin, butalbital, and caffeine.

In some embodiments, the contemplated compositions comprising a plurality of multiparticulates comprise one or more additional excipients that are combined with the multiparticulates. The one or more additional excipients comprise diluents, lubricants, gel forming excipients, and combinations thereof. In other embodiments, each multiparticulate comprises optional excipients including, but are not limited to diluents, binders, lubricants, disintigrants, colorants, plasticizers and the like.

Diluents, also termed "fillers," are typically necessary to increase the bulk of a solid dosage form so that a practical size is provided for compression of tablets. Examples of diluents include cellulose, dry starch, microcrystalline cellulose, dicalcium phosphate, calcium sulfate, sodium chloride confectioner's sugar, compressible sugar, dextrates, dextrin, dextrose, sucrose, mannitol, powdered cellulose, sorbitol, and lactose.

Binders are used to impart cohesive qualities powdered materials and can include materials such as starch, gelatin, sugars, natural and synthetic gums, polyethylene glycol, ethylcellulose, methylcellulose, hydroxypropylmethyl-cellulose, carboxymethylcellulose, waxes and polyvinyl pyrrolidone.

Lubricants are used to facilitate tablet and capsule manufacture. Examples of lubricants include talc, magnesium stearate, zinc stearate, calcium stearate, hydrogenated vegetable oils stearic acid, sodium stearyl fumarate, sodium benzoate, sodium acetate, leucine, sodium oleate, sodium lauryl sulfate, magnesium lauryl sulfate and polyethylene glycol.

Disintegrants can be added to pharmaceutical formulations in order to facilitate "breakup" or disintegration after administration. Materials used for this purpose include starches, clays, celluloses, aligns, gums, and cross-linked polymers.

A plasticizer may be included in coating materials to alter their mechanical properties. Examples of plasticizers include benzyl benzoate, chlorobutanol, dibutyl sebacate, diethyl phthalate, glycerin, mineral oil, polyethylene glycol, sorbitol, triacetin, triethyl citrate, glycerol, etc.

One or more surfactants may also be added to the final dosage form to modulate the release of drug from the multiparticulate composition. Examples include, but are not limited to, lecithin, sodium dodecyl sulfate, poloxamer, Cremophor, polysorbates, and polyoxyglycerides.

In addition to the additives above, coloring and flavoring agents may also be incorporated into the composition. Selection of excipients and the amounts used may be readily determined by the formulation scientist based upon experience and consideration of standard procedures and reference works in the field.

In one embodiment, the cured microparticles or cured formulated microparticles of the present disclosure exhibit a change in the mean percent drug released at the 4 hour dissolution time point after storage for 6 months at 25° C. and 60% RH that is within about 15%, about 10%, about 5%, or about 2.5%, when dissolution is conducted using USP Apparatus I in pH 4.5 sodium acetate buffer supplemented with 0.03% Tween 20. In one embodiment, the cured microparticles or cured formulated microparticles of the present disclosure exhibit a change in the mean percent drug released at the 4 hour dissolution time point after storage for 6 months at 25° C. and 60% RH within about 15%, 14%, 13%, 12%, 11%, 10%, 9.5%, 9%, 8.5%, 8%, 7.5%, 7%, 6.5%, 6%, 5.5%, 5%, 4.5%, 4%, 3.5%, 3%, 2.5%, 2%, or 1.5%.

In one embodiment, the pharmaceutical composition of the present disclosure provides an extended-release of the drug upon administration.

Process for Making the Pharmaceutical Compositions

The present disclosure provides a process of making a pharmaceutical composition designed to reduce the potential for improper administration of drugs that are subject to abuse. In one embodiment, the process involves forming drug containing microparticles. In another embodiment, the process involves a curing step which provides improved dissolution stability of the pharmaceutical compositions.

In one embodiment, the process of the present disclosure for making the pharmaceutical composition comprises the steps of: a) mixing one or more drugs, one or more pharmaceutically acceptable waxes, and one or more pharmaceutically acceptable fatty acids at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours.

Step (a) can comprise any suitable method of combining one or more fatty acids, one or more drugs, and one or more pharmaceutically acceptable waxes, in any order, at a temperature sufficient to form a substantially homogenous melt comprising fatty acid salts dissolved, at least in part, in the one or more pharmaceutically acceptable waxes. By way of non-limiting examples, the one or more drugs, the one or more fatty acids and the one or more pharmaceutically acceptable fatty acids can be combined together at a temperature sufficient to form a substantially homogeneous melt; alternatively the one or more drugs can first be reacted with one or more fatty acids to form fatty acid salts of the one or more drugs, then combined with the one or more pharmaceutically acceptable waxes and, optionally, one more other excipients, at a temperature sufficient to form a substantially homogeneous melt; or alternatively the one or more fatty acids, the one or more drugs, the one or more pharmaceutically acceptable waxes, and, optionally, the one or more other excipients, can be combined sequentially in any order at a temperature sufficient to form a substantially homogeneous melt, etc. Any combination or permutation of combining the one or more fatty acids, one or more drugs, and one or more pharmaceutically acceptable waxes and excipients is acceptable provided that the end result is the formation of a substantially homogeneous melt comprising a fatty acid salt homogeneously dispersed, at least in part, in the pharmaceutically acceptable wax(es).

In a further embodiment, the microparticles disclosed herein can further comprise an additional phase dispersed therein. This additional phase can include solid excipients, such as pore formers, surfactants, anti-static agents, anti-tack agents, lubricants, fillers etc. However, the fatty acid salts or complexes of the one or more drugs are substantially homogeneously dispersed or dissolved in the pharmaceutically acceptable wax(es).

In one embodiment, the minimum temperature sufficient to form a substantially homogeneous melt in step a) is about 50° C. In one embodiment, the minimum temperature sufficient to form a substantially homogeneous melt is about 60° C. In another embodiment, the minimum temperature sufficient to form a substantially homogeneous melt is about 70° C. In another embodiment, the minimum temperature sufficient to form a substantially homogeneous melt is about 80° C. In some embodiments, the temperature sufficient to form a substantially homogeneous melt is experimentally determined by slowly increasing the temperature with mixing. In some embodiments the substantially homogeneous melt is a true solution in which all components are in a liquid or dissolved state.

In one embodiment of the process disclosed herein, forming solid microparticles from the substantially homogeneous melt in step b) is carried out by feeding the melt from step a) onto a spinning disk. For example, the substantially homogeneous melt can be pumped (e.g., with a gear pump) through a heated feed line which dispenses the melt onto a rapidly spinning disk (e.g., a spinning disk atomizer), at a speed sufficient to break the melt into a spray of droplets of the desired particle size range. The droplets rapidly solidify and are collected in an enclosure to provide suitable particles, e.g. microparticles. The process may result in substantially spherical particles in which case they may be referred to as microspheres. Sieving of microparticles to produce the desired size range may also be carried out.

In other embodiments, step b) is carried out by spraying the melt from step a) using any number of congealing devices, including an ultrasonic nozzle, a pressure nozzle or a 2-fluid nozzle. Spray configurations may include top down configurations and fountain configurations whereby the melt is sprayed and atomized in an upward direction. Standard enclosures for collection of the solid microparticles include stainless steel and pharmaceutically acceptable plastic vessels and enclosures.

In other embodiments solid microparticles are formed from an extrusion process. In yet a further embodiment, solid microparticles are formed by solidifying the melt into a solid slab and subsequently milling to form suitable microparticles. Sieving of microparticles to produce the desired size range may also be carried out. Other processes, known in the pharmaceutical arts, may be used to produce microparticles of a desired size distribution from the hot melt.

The microparticles of the present invention are characterized by a median particle size of less than about 3000 microns. In some embodiments the microparticles are characterized by a median particle size of less than about 1000 microns. In some embodiments the microparticles of the present invention are characterized by a median particle size of less than about 700 microns, about 600 microns, about 500 microns, about 400 microns, about 300 microns or about 200 microns, inclusive of all values, ranges, or subranges therebetween. In some embodiments the microparticles of the present invention are characterized by a median particle size of about 300 microns.

As described herein, the term "curing" refers to heating or maintaining the compositions of the present invention at defined temperature(s) for a defined period of time as described herein.

Curing, as described herein, can be carried out at any time after preparation of the microparticles. For example, the curing steps described herein may be conducted on microparticles directly, or may be conducted on microparticles that have been further formulated. In addition, curing can be carried out on the finished unit dosage form, e.g., formulated or unformulated microparticles filled into capsules or compressed into a tablet. For example, in some embodiments microparticles are blended or formulated with external excipients, and the curing is conducted on the blended or formulated microparticles. In other embodiments the blended or formulated microparticles may be further encapsulated prior to curing. In yet further embodiments the blended microparticles may be compressed into tablets prior to curing.

In one embodiment of the process disclosed herein, curing the solid microparticles or formulated microparticles in step c) is carried out by a single-stage curing process, by a 2-stage curing process, or by a multi-stage process. In the single-stage curing process the solid microparticles are held at a single temperature that is at or below the inversion temperature for an appropriate time as experimentally determined. A 2-stage curing process utilizes two different curing temperatures for appropriate time(s) as experimentally determined. A 3-stage curing process utilizes three curing temperatures, wherein the first and the third may be same or different. A 4-stage curing process utilizes four curing temperatures, wherein non-consecutive stages can have the same or different temperatures, e.g., the first and the third or the first and the fourth. Additional curing stages can be applied as needed. A gradual temperature ramp may also be applied over time. However, at least one stage should be carried out at a temperature at or below the inversion temperature, for a time sufficient to reduce the change in the dissolution profile after storing for 6 months at 25° C. and 60% RH when compared to otherwise identical uncured microparticles after storing for 6 months at 25° C. and 60% RH.

In one embodiment, the process disclosed herein requires a 1-stage curing process. In another embodiment, the process disclosed herein requires a 2-stage curing process.

In one embodiment of the process disclosed herein, curing the solid microparticles takes place at a temperature within the range of 25° C. up to and including the inversion temperature. In another embodiment, the curing process takes place at a temperature falling within the range between 25° C. to about 60° C. or from 25° C. to about 50° C. or from about 25° C. to about 36° C., or from about 30° C. to about 45° C. In one embodiment of the disclosed process, the curing takes place at about 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, or about 60° C.

In one embodiment, the inversion temperature is about 34, 35, 36, 37, or 38° C. In some embodiments, the curing process disclosed herein is a 2-stage process which involves heating the microparticles to a first temperature above the inversion temperature and subsequently a second temperature at or below the inversion temperature.

In one embodiment, the 2-stage curing process is carried out at a first temperature of about 37, 38, 39, 40, 41, or 42° C. and a second temperature of about 28, 29, 30, 31, 32, 33, 34, 35, or 36° C. In one embodiment, the 2-stage curing process is carried out at a first temperature of about 40° C. and a second temperature of about 30° C. In another embodiment, the 2-stage curing process is carried out at a first temperature of about 38° C. and a second temperature of about 32° C.

In one embodiment of the process disclosed herein, the time sufficient for curing is the time required to reduce the change in the dissolution profile for cured compositions after storing for 6 months at 25° C. and 60% RH when compared with the change observed for otherwise identical uncured compositions after storing for 6 months at 25° C. and 60% RH when dissolution is conducted using USP Apparatus I in pH 4.5 sodium acetate buffer supplemented with 0.03% Tween 20. This time can be determined experimentally. To do this, a baseline change for the uncured composition must be established by comparing the dissolution profile for the uncured composition at the time of manufacture with the dissolution profile following storage for 6 months at 25° C. and 60% RH. The goal of curing is to improve upon, or reduce, this uncured baseline change. To determine the appropriate curing time, the same composition should be cured at a temperature between 25° C. and the inversion temperature, for various times. Subsequently, the dissolution profile of the cured composition at the time of manufacture should be compared with the dissolution profile following storage for 6 months at 25° C. and 60% RH. An appropriate time is established when the change in the cured composition following storage is less than the corresponding change for the uncured composition. In another embodiment, the time sufficient for curing is a minimum of about 48 hours. In one embodiment, the time sufficient for curing is about 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the time sufficient for curing is about 7 days.

In one embodiment of the process disclosed herein, the time sufficient for curing is the total time, e.g., combined time cured at first temperature and second temperature in a multi-stage curing process.

In one embodiment, the cured microparticles or cured formulated microparticles prepared by the disclosed process exhibit a change in the mean percent drug released at the 4 hour dissolution time point after storage for 6 months at 25° C. and 60% RH that is less than about 15%, about 10%, about 5%, or about 2.5%, when dissolution is conducted using USP Apparatus I in pH 4.5 sodium acetate buffer supplemented with 0.03% Tween 20. In one embodiment, the cured microparticles or cured formulated microparticles of the present disclosure exhibit a change in the mean percent drug released at the 4 hour dissolution time point after storage for 6 months at 25° C. and 60% RH within about 15%, 14%, 13%, 12%, 11%, 10%, 9.5%, 9%, 8.5%, 8%, 7.5%, 7%, 6.5%, 6%, 5.5%, 5%, 4.5%, 4%, 3.5%, 3%, 2.5%, 2%, or 1.5%.

In one embodiment of the present disclosure, a pharmaceutical composition prepared by any one of the processes disclosed herein is provided. In another embodiment of the present disclosure, a capsule comprising a pharmaceutical composition prepared by any one of the processes disclosed herein is provided.

In a further embodiment of the present disclosure, a pharmaceutical composition comprising oxycodone and myristic acid prepared by any one of the processes disclosed herein is provided where the inversion temperature is about 36° C. In another embodiment of the present disclosure, a capsule comprising a pharmaceutical composition comprising oxycodone and myristic acid prepared by any one of the processes disclosed herein is provided where the inversion temperature is about 36° C.

Method of Treatment

The present disclosure provides a method of administering any one of the pharmaceutical compositions or a capsule as disclosed herein to a subject in need thereof. In some embodiments, the method includes treatment or management of pain. In one embodiment, the pain to be treated can be severe enough to require daily, around-the-clock, long-term opioid treatment and for which alternative treatment options are inadequate. In one embodiment, the disclosed method provides a therapeutically effective amount of the one or more drugs to a subject in need thereof.

For the purposes of this disclosure, the composition of the present disclosure can be formulated for administration by a variety of means. In one embodiment, the administration of the method disclosed herein is orally. In one embodiment, a solid oral dosage form, such as a capsule can be used to administer to a subject in need thereof.

EXAMPLES

Material and Methods

Unless otherwise noted, the following material and equipment were used as received or under standard operating conditions. Laboratory ovens and/or stability chambers were used to cure microspheres. Unless otherwise noted, a manual encapsulator or an automated encapsulator was used to fill capsules with blend.

Microparticles

Excipients were first melted in a stainless steel jacketed vessel. The active pharmaceutical ingredient (API) was dissolved in the melt with stirring. The melt was then processed into microspheres by one of the following procedures:

A) The melt was fed to a spinning disk. The disk rotates at a speed designed to produce solid microspheres of the desired particle size distribution.

B) The melt was forced through a plastic atomization nozzle mounted on a plastic syringe. The syringe plunger was pressed through the barrel using a pneumatic piston. The piston was activated with an air pressure sufficient to press the melt through the barrel at a speed high enough to atomize the melt and produce microspheres.

Curing, blending and encapsulation (where applicable) were carried out as noted in the individual examples.

Dissolution Test

Product dissolution is conducted using USP Apparatus with media (900 mL, pH 4.5 sodium acetate buffer, 0.03% Tween 20) pre-heated to 37° C. For capsule dissolution, USP Apparatus I (baskets) at 100 rpm was utilized.

Example 1: Stability of Uncured Microspheres at Different Conditions of Temperature and Humidity Microspheres containing oxycodone, myristic acid, beeswax, carnauba wax and stearoyl polyoxyl-32 glycerides were produced using spinning disk atomization as described above. The microspheres were blended with colloidal silicon dioxide and magnesium stearate and machine encapsulated to form capsules. Capsules were packaged in high-density polyethylene bottles and placed in stability chambers according to ICH conditions; long-term (25° C./60% RH), intermediate (30° C./65% RH) and accelerated (40° C./75% RH) conditions were used in the study. The dissolution profile of the capsules was determined at the time of manufacture and periodically while on stability. The % drug released as a function of time in dissolution is shown in FIG. 1 at time zero and after storage for 3 months at all 3 ICH stability conditions.

The behavior of the microspheres was unexpected on stability. The dissolution profile of the uncured microspheres tends to increase (i.e., faster dissolution) on storage at 40° C./75% RH and decrease (i.e., slower dissolution) on storage at 25° C./60% RH or 30° C./65% RH. Given that the microspheres are hydrophobic and absorb virtually no moisture irrespective of humidity level, i.e. dissolution is not impacted by humidity level, the data suggests the presence of an "inversion temperature", between 30° C. and 40° C., at which the dissolution behavior reverses and rather than tending to decrease, will tend to increase. Furthermore, the decrease observed at long-term conditions (predictive of long-term room temperature storage in a warehouse, pharmacy or medicine cabinet) is greater than desired after 3 months (eg, approximately 15% lower at the 4 hour dissolution time point).

Example 2: Establishment of Inversion Temperature

On the basis of stability data shown in Example 1, the dissolution behavior of microspheres containing oxycodone, myristic acid, beeswax, carnauba wax and stearoyl polyoxyl-32 glycerides was investigated at temperatures falling between 30° C. and 40° C. Specifically, the microspheres were exposed to elevated temperatures between 32° C.-36° C. after 2 days (48 hours) and 6-7 days. FIGS. 2A and 2B display the impact of curing temperature at each individual dissolution time point. FIG. 2A shows the impact of curing for 2 days and FIG. 2B shows the impact of curing for 6-7 days. Both graphs also show the dissolution results for the uncured formulation as a control. After 2 days of curing at 32° C.-34° C., there is only a slight reduction in dissolution versus the uncured formulation. A further drop in dissolution is generally observed with increasing temperature from 34° C. to 36° C., especially at the 8-hour and longer time points.

Changes after 6-7 days of curing are not linear with temperature. After curing for 7 days at 32° C., dissolution decreases significantly below the dissolution of uncured material. Dissolution of uncured formulation at the 2-hour, 4-hour, 8-hour and 12-hour dissolution time points is 30.7%, 48.1%, 68.2%, and 83.2%, respectively. The corresponding dissolution after curing for 7 days at 32° C. is 27.3%, 42.04%, 60.3%, and 75.5%, respectively. After curing at 33° C. or 34° C., dissolution remained below that of uncured material. The dissolution is minimal around 35° C. where it was now lower than at 32° C. The slowest dissolution rate was thus observed after 7 days at 35° C.; however, there was an abrupt change in behavior between 35° C. and 36° C., with the dissolution starting an increase to a level that is higher than the dissolution of uncured control material.

The behavior between 32° C. and 36° C. was qualitatively consistent with that observed in FIG. 1, i.e. dissolution decreases at low curing temperatures and increases at high curing temperatures; however, between these temperatures the dissolution behavior was non-linear and exhibited an inflection point around approximately 36° C. This is defined as the "inflection or inversion temperature". This explains the observed increase in dissolution in Example 1 with storage at 40° C., above the inversion temperature.

Example 3: Single-Stage Curing Process

Based on the dissolution behavior for microspheres containing oxycodone, myristic acid, beeswax, carnauba wax and stearoyl polyoxyl-32 glycerides after exposure to different temperatures, studies to implement a curing process were conducted. The hypothesis was that curing at a temperature above 25° C., but below the inversion temperature (35-36° C.), would improve the dissolution stability of the microspheres when stored at ICH long-term conditions (25° C./75% RH). The process consisted of a single-stage (ie, a single temperature) and a duration of 30 days. For these studies, microspheres were blended with colloidal silicon dioxide and magnesium stearate and encapsulated prior to curing. Uncured microspheres that were similarly blended and encapsulated were also tested as a control.

The dissolution stability behavior of uncured capsules that were stored at 25° C./60% RH is shown in FIG. 3A. A relatively large drop in dissolution is observed. Dissolution drops by 15% at the 4-hour time point on storage for 6 months at 25° C./60% RH.

The dissolution stability behavior of capsules that were cured at 34° C., 30° C., or 32° C. and then stored at 25° C./60% RH for 6 month is shown in FIG. 3B, FIG. 3C, and FIG. 3D, respectively. Curing below the inversion temperature (34° C., 32° C., and 30° C.) results in considerably more stable product than no curing (compare to FIG. 3A).

Example 4: Two-Stage Curing Process

A 2-stage curing process was also tested. In the 2-stage curing process, the product is held first at a relatively high temperature above the inversion temperature followed by temperature below the inversion temperature.

A 2-stage curing process which consists of holding the microspheres at 40° C. for 4 days followed by a period of 3 days at 30° C. was evaluated (40° C./4 d; 30° C./3 d). These conditions were applied to the uncured microspheres of Example 3, followed by blending with colloidal silicon dioxide and magnesium stearate, and encapsulation. The capsules were tested for dissolution at time zero and following storage for 6 months at 25° C./60% RH. Comparison of data in FIGS. 3E and 3A show that curing for 4 days at 40° C. followed by 3 days at 30° C. results in a more stable formulation versus uncured formulation stored for 6 months at 25° C./60% RH.

Table 1 summarizes the difference in dissolution between time zero (i.e., measured after manufacture) and after 6 months of storage at 25° C. and 65% RH for Example 3 compositions. As shown in the table, the difference is reduced for all curing conditions relative to the microsphere formulation that was not subjected to curing (control condition). For example, at the 4 hour dissolution time point the difference is reduced by at least half for all curing conditions.

TABLE 1

| Dissolution | Change in dissolution (% Released at Time Zero-% Released after 6 months at 25° C./65% RH) | | | | | |
| --- | --- | --- | --- | --- | --- | --- |
| Time Point (hours) | Control- No Curing | Curing at 30° C. (1 month) | Curing at 32° C. (1 month) | Curing at 34° C. (1 month) | Curing at 36° C. (1 month) | Curing at 40° C. (4 days), 30° C. (3 days) |
| 1 | 8.4 | 0.6 | −0.4 | 1.5 | 2.3 | 6.0 |
| 2 | 11.0 | 1.6 | 0.2 | 2.0 | 4.4 | 7.1 |
| 4 | 14.7 | 2.3 | 0.2 | 3.0 | 6.1 | 7.0 |
| 8 | 15.5 | 3.0 | 0.3 | 3.3 | 6.8 | 6.3 |
| 12 | 13.4 | 2.8 | 0.2 | 3.3 | 7.4 | 4.6 |
| 16 | 9.4 | 3.1 | 0.6 | 3.1 | 2.1 | 5.9 |
| 20 | 5.1 | 2.9 | 0.01 | 3.4 | 1.5 | −0.4 |
| 24 | 2.6 | 2.6 | −0.8 | 2.4 | 2.6 | −3.0 |

Example 5: Inversion Temperature for Formulations Comprising Drug, Stearic Acid, and Waxes The dissolution behavior of a microsphere formulation comprising oxycodone, stearic acid and waxes before and after single stage curing at 50° C. is shown in FIG. 4A. Dissolution decreases when the formulation is cured at 50° C.

The dissolution behavior of a microsphere formulation comprising oxymorphone, stearic acid and waxes before and after curing at 50° C. is shown in FIG. 4B. Here again, dissolution decreases when curing at 50° C.

The dissolution behavior of a microsphere formulation comprising oxymorphone, stearic acid and waxes before and after curing at 55° C. or 60° C. is shown in FIG. 4C. Dissolution increases when curing at 55° C. or 60° C. FIG. 4A, FIG. 4B, and FIG. 4C indicate that the inversion temperature is between 50° C. and 55° C. when using stearic acid. These results indicate that the inversion temperature can increase with increasing fatty acid molecular weight or with a change in the formulation.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A pharmaceutical composition comprising solid microparticles or formulated microparticles prepared by:
   (a) preparing a mixture at a temperature sufficient to form a melt comprising:
      (i) oxycodone, myristic acid, beeswax and carnauba wax, or
      (ii) oxycodone in the form of a myristic acid salt, beeswax and carnauba wax;
   (b) forming solid microparticles from the melt;
   (c) optionally further formulating the solid microparticles with additional pharmaceutically acceptable excipients to provide formulated microparticles, and
   (d) curing the solid microparticles or the formulated microparticles at one or more curing temperatures from 26° C. to 38° C., for a minimum of about 48 hours to provide cured solid microparticles or cured formulated microparticles.

2. The pharmaceutical composition of claim 1 wherein the mixture of step (a) further includes stearoyl polyoxyl-32 glycerides.

3. The pharmaceutical composition of claim 1, wherein the solid microparticles or the formulated microparticles are cured at one or more curing temperatures from 26° C. to 36° C.

4. The pharmaceutical composition of claim 1, wherein the solid microparticles or the formulated microparticles are cured at one or more curing temperatures from 26° C. to 34° C.

5. The pharmaceutical composition of claim 1, wherein the solid microparticles or the formulated microparticles are cured at one or more curing temperatures from 26° C. to 32° C.

6. The pharmaceutical composition of claim 1, wherein the solid microparticles or the formulated microparticles are cured at one or more curing temperatures from 26° C. to 30° C.

7. The pharmaceutical composition of claim 1, wherein the solid microparticles or the formulated microparticles are cured at one or more curing temperatures from 26° C. to 28° C.

8. The pharmaceutical composition of claim 1, wherein the solid microparticles or the formulated microparticles are cured at one or more curing temperatures from 27° C. to 36° C.

9. The pharmaceutical composition of claim 1, wherein the solid microparticles or the formulated microparticles are cured at one or more curing temperatures from 28° C. to 38° C.

10. The pharmaceutical composition of claim 1, wherein the solid microparticles or the formulated microparticles are cured at one or more curing temperatures from 28° C. to 36° C.

11. The pharmaceutical composition of claim 1, wherein the solid microparticles or the formulated microparticles are cured at one or more curing temperatures from 28° C. to 35° C.

12. The pharmaceutical composition of claim 1, wherein the solid microparticles or the formulated microparticles are cured at one or more curing temperatures from 28° C. to 34° C.

13. The pharmaceutical composition of claim 1, wherein the solid microparticles or the formulated microparticles are cured at one or more curing temperatures from 28° C. to 33° C.

14. The pharmaceutical composition of claim 1, wherein the solid microparticles or the formulated microparticles are cured at one or more curing temperatures from 28° C. to 32° C.

15. The pharmaceutical composition of claim 1, wherein the solid microparticles or the formulated microparticles are cured at one or more curing temperatures from 28° C. to 30° C.

16. The pharmaceutical composition of claim 1, wherein the solid microparticles or the formulated microparticles are cured at one or more curing temperatures from 30° C. to 38° C.

17. The pharmaceutical composition of claim 1, wherein the solid microparticles or the formulated microparticles are cured at one or more curing temperatures from 30° C. to 36° C.

18. The pharmaceutical composition of claim 1, wherein the solid microparticles or the formulated microparticles are cured at one or more curing temperatures from 30° C. to 34° C.

19. The pharmaceutical composition of claim 1, wherein the solid microparticles or the formulated microparticles are cured at one or more curing temperatures from 30° C. to 32° C.

20. The pharmaceutical composition of claim 1, wherein the solid microparticles or the formulated microparticles are cured at one or more curing temperatures from 32° C. to 38° C.

21. The pharmaceutical composition of claim 1, wherein the solid microparticles or the formulated microparticles are cured at one or more curing temperatures from 32° C. to 36° C.

22. The pharmaceutical composition of claim 1, wherein the solid microparticles or the formulated microparticles are cured at one or more curing temperatures from 32° C. to 34° C.

23. The pharmaceutical composition of claim 1, wherein the solid microparticles or the formulated microparticles are cured at one or more curing temperatures from 34° C. to 38° C.

24. The pharmaceutical composition of claim 1, wherein the solid microparticles or the formulated microparticles are cured at one or more curing temperatures from 34° C. to 36° C.

25. The pharmaceutical composition of claim 1, wherein the solid microparticles or the formulated microparticles are cured at one or more curing temperatures from 36° C. to 38° C.

26. The pharmaceutical composition of claim 1, wherein the solid microparticles are cured at 26° C.

27. The pharmaceutical composition of claim 1, wherein the solid microparticles are cured at 27° C.

28. The pharmaceutical composition of claim 1, wherein the solid microparticles are cured at 28° C.

29. The pharmaceutical composition of claim 1, wherein the solid microparticles are cured at 29° C.

30. The pharmaceutical composition of claim 1, wherein the solid microparticles are cured at 30° C.

31. The pharmaceutical composition of claim 1, wherein the solid microparticles are cured at 31° C.

32. The pharmaceutical composition of claim 1, wherein the solid microparticles are cured at 32° C.

33. The pharmaceutical composition of claim 1, wherein the solid microparticles are cured at 33° C.

34. The pharmaceutical composition of claim 1, wherein the solid microparticles are cured at 34° C.

35. The pharmaceutical composition of claim 1, wherein the solid microparticles are cured at 35° C.

36. The pharmaceutical composition of claim 1, wherein the solid microparticles are cured at 36° C.

37. The pharmaceutical composition of claim 1, wherein the solid microparticles are cured at 37° C.

38. The pharmaceutical composition of claim 1, wherein the solid microparticles are cured at 38° C.

39. The pharmaceutical composition of claim 1, wherein the solid microparticles or the formulated microparticles are cured for about 3 days.

40. The pharmaceutical composition of claim 1, wherein the solid microparticles or the formulated microparticles are cured for about 4 days.

41. The pharmaceutical composition of claim 1, wherein the solid microparticles or the formulated microparticles are cured for about 5 days.

42. The pharmaceutical composition of claim 1, wherein the solid microparticles or the formulated microparticles are cured for about 6 days.

43. The pharmaceutical composition of claim 1, wherein the solid microparticles or the formulated microparticles are cured for about 7 days.

44. The pharmaceutical composition of claim 1, wherein the solid microparticles or the formulated microparticles are cured for about 8 days.

45. The pharmaceutical composition of claim 1, wherein the solid microparticles or the formulated microparticles are cured for about 9 days.

46. The pharmaceutical composition of claim 1, wherein the solid microparticles or the formulated microparticles are cured for about 10 days.

47. The pharmaceutical composition of claim 1, wherein the solid microparticles or the formulated microparticles are cured for about 11 days.

48. The pharmaceutical composition of claim 1, wherein the solid microparticles or the formulated microparticles are cured for about 12 days.

49. The pharmaceutical composition of claim 1, wherein the solid microparticles or the formulated microparticles are cured for about 13 days.

50. The pharmaceutical composition of claim 1, wherein the solid microparticles or the formulated microparticles are cured for about 14 days.

51. The pharmaceutical composition of claim 1, comprising myristic acid in about 30 wt. % to about 70 wt. % of the pharmaceutical composition.

52. The pharmaceutical composition of claim 1, comprising myristic acid in about 40 wt. % to about 60 wt. % of the pharmaceutical composition.

53. The pharmaceutical composition of claim 1, wherein the combination of beeswax and carnauba wax comprises about 20 wt. % to about 60 wt. % of the pharmaceutical composition.

54. The pharmaceutical composition of claim 1, wherein the combination of beeswax and carnauba wax comprises about 30 wt. % to about 50 wt. % of the pharmaceutical composition.

55. The pharmaceutical composition of claim 1, comprising:
   a. about 9 mg to about 72 mg oxycodone or an equivalent amount of a myristic acid salt thereof;
   b. about 30 wt. % to about 70 wt. % of myristic acid; and
   c. about 20 wt. % to about 60 wt. % of a combination of beeswax and carnauba wax.

56. The pharmaceutical composition of claim 1, comprising:
   a. about 9 mg to about 72 mg oxycodone or an equivalent amount of a myristic acid salt thereof;
   b. about 40 wt. % to about 60 wt. % of myristic acid; and
   c. about 30 wt. % to about 50 wt. % of a combination of beeswax and carnauba wax.

57. The pharmaceutical composition of claim 1, comprising:
   a. about 9 mg to about 36 mg oxycodone or an equivalent amount of a myristic acid salt thereof;
   b. about 40 wt. % to about 60 wt. % of myristic acid; and
   c. about 30 wt. % to about 50 wt. % of a combination of beeswax and carnauba wax.

58. A capsule comprising the pharmaceutical composition of claim 1.

59. A capsule comprising the pharmaceutical composition of claim 55.

60. A capsule comprising the pharmaceutical composition of claim 56.

61. A capsule comprising the pharmaceutical composition of claim 57.

62. A method of treating pain comprising administering the pharmaceutically composition of claim 1 to a patient in need thereof.

63. A method of treating pain comprising administering the pharmaceutical composition of claim 55 to a patient in need thereof.

64. A method of treating pain comprising administering the pharmaceutical composition of claim 57 to a patient in need thereof.

65. A method of treating pain comprising administering the capsule of claim 58 to a patient in need thereof.

66. A method of treating pain comprising administering the capsule of claim 59 to a patient in need thereof.

67. A method of treating pain comprising administering the capsule of claim 61 to a patient in need thereof.

* * * * *